(12) United States Patent
Epshtein et al.

(10) Patent No.: US 8,865,163 B2
(45) Date of Patent: Oct. 21, 2014

(54) PHARMACEUTICAL COMPOSITIONS AND METHODS OF TREATMENT

(75) Inventors: Oleg Iliich Epshtein, Moscow (RU); Svetlana Alexandrovna Sergeeva, Moscow (RU); Liudmila Fyodorovna Dolgovyh, Chelyabinsk (RU); Irina Anatolievna Kheyfets, Moskovskaya (RU); Julia Leonidovna Dugina, Moscow (RU); Julia Alexandrovna Zabolotneva, Moscow (RU); Sergey Alexandrovich Tarasov, Odintsovsky (RU)

(73) Assignee: Oleg I. Epshtein (RU)

( * ) Notice: Subject to any disclaimer, the term of this patent is extended or adjusted under 35 U.S.C. 154(b) by 14 days.

(21) Appl. No.: 13/135,893

(22) Filed: Jul. 15, 2011

(65) Prior Publication Data

US 2013/0017202 A1    Jan. 17, 2013

(30) Foreign Application Priority Data

Jul. 15, 2010 (RU) .................. 2010129289
Jul. 21, 2010 (RU) .................. 2010130350
Jun. 2, 2011 (RU) .................. 2011122407

(51) Int. Cl.

| A61K 39/395 | (2006.01) |
| C07K 16/28 | (2006.01) |
| C07K 16/24 | (2006.01) |
| A61K 41/00 | (2006.01) |
| A61Q 19/06 | (2006.01) |
| A61K 8/64 | (2006.01) |
| A61K 39/00 | (2006.01) |

(52) U.S. Cl.
CPC ............. *C07K 16/28* (2013.01); *A61K 2800/78* (2013.01); *C07K 16/24* (2013.01); *A61K 41/0004* (2013.01); *A61K 2039/505* (2013.01); *A61Q 19/06* (2013.01); *A61K 2039/545* (2013.01); *A61K 2039/507* (2013.01); *A61K 8/64* (2013.01)
USPC .................................................... 424/130.1

(58) Field of Classification Search
CPC ................................................. A61K 41/0004
See application file for complete search history.

(56) References Cited

U.S. PATENT DOCUMENTS

| 5,849,528 | A | 12/1998 | Hillman et al. |
| 7,229,648 | B2 | 6/2007 | Dreyer |
| 7,572,441 | B2 | 8/2009 | Epshtein et al. |
| 7,582,294 | B2 | 9/2009 | Epshtein et al. |
| 7,700,096 | B2 | 4/2010 | Epshtein et al. |
| 7,815,904 | B2 | 10/2010 | Epshtein et al. |
| 7,923,009 | B2 | 4/2011 | Epshtein et al. |
| 8,066,992 | B2 | 11/2011 | Epshtein |
| 8,168,182 | B2 | 5/2012 | Epshtein |
| 8,178,498 | B1 | 5/2012 | Ephstein |
| 8,241,625 | B2 | 8/2012 | Epshtein et al. |
| 8,524,229 | B2 | 9/2013 | Epshtein et al. |
| 8,535,664 | B2 | 9/2013 | Epshtein et al. |
| 8,617,555 | B2 | 12/2013 | Epshtein |
| 8,637,030 | B2 | 1/2014 | Epshtein |
| 8,637,034 | B2 | 1/2014 | Epshtein |
| 2005/0100513 | A1 | 5/2005 | Watkins et al. |
| 2010/0166762 | A1 | 7/2010 | Epshtein |
| 2012/0219556 | A1 | 8/2012 | Epshtein |
| 2012/0258146 | A1 | 10/2012 | Epshtein |
| 2012/0321672 | A1 | 12/2012 | Epshtein |
| 2013/0004574 | A1 | 1/2013 | Epshtein |
| 2013/0058981 | A1 | 3/2013 | Epshtein |
| 2013/0058982 | A1 | 3/2013 | Epshtein |

FOREIGN PATENT DOCUMENTS

| CN | 101495143 A | 7/2009 |
| CN | 101528733 A | 9/2009 |
| EP | 1547612 A1 | 6/2005 |
| EP | 1550460 A1 | 7/2005 |
| EP | 2036574 A1 | 3/2009 |
| RU | 2156621 C1 | 9/2000 |
| RU | 2437678 C2 | 12/2011 |
| WO | WO 2008070305 A2 | 6/2008 |
| WO | WO 2008122618 A1 | 10/2008 |

OTHER PUBLICATIONS

Shang A et al.: "Are the clinical effects of homoeopathy placebo effects? Comparative study of placebo-controlled trials of homoeopathy and allopathy", The Lancet, Lancet Limited. London, GB, vol. 366, No. 9487, Aug. 27, 2005, pp. 726-732.
Vickers A J: "Clinical trials of homeopathy and placebo: Analysis of a scientific debate", Journal of Alternative and Complementary Medicine, Mary Ann Liebert, New York, NY, US ,vol. 6, No. 1, Feb. 1, 2000, pp. 49-56.
Jonas Wayne B et al: "A critical overview of homeopathy", Annals of Internal Medicine, New York, NY; US, US, vol. 138, No. 5, Mar. 4, 2003 pp. 393-399.
Notification of Transmittal of International Search Report and Written Opinion dated Feb. 13, 2012 for corresponding International Patent Application No. PCT/IB2011/002404, (Feb. 13, 2012).
International Search Report dated Feb. 13, 2012 for corresponding International Patent Application No. PCT/IB2011/002404, (Feb. 13, 2012).
Written Opinion of the International Searching Authority for corresponding International Patent Application No. PCT/IB2011/002404, (Feb. 13, 2012).

(Continued)

*Primary Examiner* — Ilia Ouspenski
(74) *Attorney, Agent, or Firm* — Pergament Gilman & Cepeda LLP

(57) ABSTRACT

The present invention provides pharmaceutical compositions comprising an activated potentiated form of an antibody to human cannabinoid receptor and use in the treatment of obesity and related metabolic disorders. The present invention further provides pharmaceutical compositions comprising an activated potentiated form of an antibody to human cannabinoid receptor and activated potentiated form of an antibody to protein S-100 for use in the treatment of addiction to psychoactive substances.

The present invention provides methods for treating obesity and related metabolic disorders and substance abuse.

11 Claims, 3 Drawing Sheets

(56) References Cited

OTHER PUBLICATIONS

Pavlov, I. F., "Effect of Antibodies Against S-100B Antigen in Ultralow Doses on Sucrose Consumption During Learing", Biophysics and Biochemistry, 2007, p. 686-688, vol. 143 No. 6.
Office Action dated Nov. 5, 2013, issued by the Swedish Patent Office for corresponding Swedish Patent Application No. 1350179-6 based on International Patent Application No. PCT/IB2011/002404.
Mackie, "Cannabinoid Receptors as Therapeutic Targets", Annual Review of Pharmacology and Toxicology, 2006, p. 101-122, vo. 46.
Bohan, et al., "Comparative Effectiveness of "Proprotien-100" Alcoholism in Treatment of Patients in Phase Formation Therapeutic Remission", Bulletin Experimental Biology and Medicine, 2003, pp. 91-96.
Machine translation of abstract of Bohan, et al., "Comparative Effectiveness of "Proprotien-100" Alcoholism in Treatment of Patients in Phase Formation Therapeutic Remission", Bulletin Experimental Biology and Medicine, 2003, pp. 91-96.
Pharmaceutical Label for Dronabinol "MARINOL", Unimed Pharmaceuticals, Inc., Oct. 2002, p. 3-10.
Hu, et al., "S100B Induces Neuronal Cell Death Through Nitric Oxide Release from Astrocytes", Journal of Neurochemistry, 1997, vol. 69, No. 6, p. 2294-2301, Lippincott-Raven Publishers, Philadelphia, PA.
Wiencken, et al., "Endothelial Nitric Oxide Synthetase (eNOS) in Astrocytes: Another Source of Nitric Oxide in Neocortex", GLIA, 1999, p. 280-290.
Voronina, et al., "Effect of Ultralow Doses of Antibodies to S-100 Protein in Animals with Impaired Cognitive Function and Disturbed Emotional and Neurological Status under Conditions of Experimental Alzheimer Disease", Bulletin of Experimental Biology and Medicine, 2009, vol. 148, suppl. 1, p. 533-535.
Duma, et al., "Tenoten in the Therapy of Patients with Moderate Cognitive Impairment", Bulletin of Experimental Biology and Medicine, 2009, vol. 148, suppl. 1, p. 353-356.
Epshtein, et al., "Psychotropic Drug Tenoten Activates Mitogen-Activated MAP/ERK Kinase Regulatory Cascade Controlling the Neuroprotective Effects", Bulletin of Experimental Biology and Medicine, 2007, vol. 144, No. 3, p. 319-321.
Barann, et al., "Direct Inhibition by Cannabinoids of Human 5-HT3A Receptors: Probable Involvement of an Allosteric Modulatory Site", British Journal of Pharmacology, 2002, vol. 137, p. 589-596.
Pavlov I. F., "Effects of Antibodies Against S-100 Antigen in Ultralow Doses (Proproten-100) on Acquisition of Avoidance Response in Rats", Bulletin of Experimental Biology and Medicine, 2004, No. 6, p. 556-558.
Castagne, et al., "Antibodies to S100 Proteins Have Anxiolytic-like Activity at Ultra-low Doses in the Adult Rat", Journal of Pharmacy and Pharmacology, 2008, p. 309-316.
Epstein O. I., "Regulatory Activity of Ultralow Doses", Bulletin of Experimental Biology and Medicine, 2003, supp. 1, p. 8-13.
Epshtein, et al., "Effects of Potentiated Antibodies to Brain Specific Protein S100 on the Dynamics of Long-Term Potentiation in Hippocampal Slices", Bulletin of Experimental Biology and Medicine, 1999, No. 3, p. 286-289.
Marenholz, et al., "S100 Proteins in Mouse and Man: From Evolution to Function and Pathology (Including an Update of the Nomenclature)", Biochemical and Biophysical Research Communications, 2004, p. 1111-1122.
Romanova, et al., "Neuroprotective Activity of Proproten in Rats with Experimental Local Photothrombosis of the Prefrontal Cortex", Bulletin of Experimental Biology and Medicine, 2005, vol. 139, No. 4, p. 404-407.
Epshtein, et al., "Effect of Potentiated Antibodies to Brain-Specific Protein S100 on the Integrative Activity of the Brain", Bulletin of Experimental Biology and Medicine, 1999, No. 5, p. 493-495.
Epstein, et al., "Improvement of Memory by Means of Ultra-Low Doses of Antibodies to S-100B Antigen", Institue of Molecular Biology and Biophysics, Siberian Department of Russian Academy of Medical Sciences, Advance Access Publication, 2006, p. 541-545, Novosibirsk, Russia.
Dugina, et al., "P.7.b.004 Anti-S100 antibodies modulate locomotor activity and exploratory behaviour of immature rats", European Neuropsychopharmacology, Oct. 1, 2007, vol. 17, p. S571, Elsevier Science Publishers BV, Amsterdam, NL.
Office Action, dated Mar. 7, 2014, issued by the Chinese Patent Office, for corresponding Foreign Patent Application No. CN 201180044227.0.
Bingham, et al., "Species-Specific in vitro Pharmacological Effects of the Cannabinoid Receptor 2 (CB2) Selective Ligand AM1241 and its Resolved Enantiomers", British Journal of Pharmacology, 2007, vol. 151, pp. 1061-1070.
Langmead, et al., "Characterisation of the Binding of [3H]-SB-674042, A Novel Nonpeptide Antagonist, to the Human Orexin-1 Receptor", British Journal of Pharmacology, 2004, vol. 141, pp. 340-346.
Laffly E., et al., "Monoclonal and Recombinant Antibodies, 30 Years After", Human Antibodies, 2005, vol. 14, N 1-2, pp. 33-55.
Heatherton, et al., "The Fagerström Test for Nicotine Dependence: a revision of the Fagerstrom Tolerance Questionnaire", British Journal of Addiction, Sep. 1991, vol. 86, Issue 9, pp. 1119-1127.
Di Marzo, et al., "Endocannabinoids: endogenous cannabinoid receptor ligands with neuromodulatory action", Trends Neurosci. 1998, vol. 21(12), pp. 521-528.
Pertwee, "Pharmacology of Cannabinoid CB1 and CB2 Receptors", 1997, Pharmacology & Therapeutics, vol. 74, No. 2, pp. 129-180.
Sung, et al., "Waist Circumference and Waist-to-Height Ratio of Hong Kong Chinese Children", 2008, BMC Public Health, 8:324, pp. 1-10.
Ackermann, et al.," S100A 1-Deficient Male Mice Exhibit Increased Exploratory Activity and Reduced Anxiety-Related Responses", BBA, 2006, pp. 1307-1319.
Hsieh, et al., "Waist-to-Height Ratio, A Simple and Practical Index for Assessing Central Fat Distribution and Metabolic Risk in Japanese Men and Women", International Journal of Obesity, 2003, vol. 27, pp. 610-616.
Price, et al., "Weight Shape, and Mortality Risk in Older Persons: Elevated Waist-Hip Ratio, Not High Body Mass Index, is Associated with a Greater Risk of Death", The American Journal of Clinical Nutrition, 2006, vol. 84, pp. 449-60.
Bray, "Pharmacologic Treatment of Obesity: Symposium Overview", Obesity Research, 1995, vol. 3, supplement 4, pp. 415-417.
McGinnis, et al., "Actual Causes of Death in the United States", JAMA, 1993, vol. 270, No. 18, pp. 2207-2212.
Clarke, "Nicotinic Receptor Blockade Therapy and Smoking Cessation", British Journal of Addiction, 1991, vol. 86, pp. 501-505.
Cinciripini, et al., "Smoking Cessation: Recent Developments in Behavioral and Pharmacologic Interventions", Oncology, 1998, vol. 12, pp. 249-256.
Diehl, et al., "Long Lasting Sex-Specific Effects Upon Behavior and S100B Levels After maternal Separation and Exposure to a Model of Post-Traumatic Stress Disorders in Rats", Brain Research, 2007, vol. 1144, pp. 107-116.
Vyatcheslav, et al., "Antibodies to Calcium-Binding S100B Protein Block the Conditioning of Long-Term Sensitization in the Terrestrial Snail", Pharmacology Biochemistry and Behavior, Nov. 2009, vol. 94, Issue 1, pp. 37-42.
West, et al., "Evaluation of the Mood and Physical Symptoms Scale (MPSS) to Assess Cigarette Withdrawal", Psychopharmacology, 2004, vol. 177, pp. 195-199.
Gershenfeld, et al., "Mapping Quantitative Trait Loci for Open-Field Behavior in Mice", Behavior Genetics, 1997, vol. 27, No. 3, pp. 210-210.
Zigmond, et al., "The Hospital Anxiety and Depression Scale", Acta Psychiatr. Scand., 1983, vol. 67, Issue 6, pp. 361-370.
Zanin, et al., "Endocannabinoid System: Prospects of Stimulation", Usp Fiziol Nauk., 2007, vol. 38(1), pp. 66-73.
MEDLINE Abstract for Zanin, et al., "Endocannabinoid System: Prospects of Stimulation", Usp Fiziol Nauk., 2007, vol. 38(1), pp. 66-73.
Frimel, "Immunologicheskie metody (Immunological Methods)", Moscow: Meditsina, 1987, p. 9-33.
Schwab, V., "Homeopathic Pharmaceutical Agents. A manual on description and preparation", Moscow, 1967.

PHARMACEUTICAL COMPOSITIONS AND METHODS OF TREATMENT

FIELD

The present invention relates to pharmaceutical compositions that can be used for the treatment of obesity and related metabolic disorders and for treating addiction to psychoactive substances, in particular nicotine.

BACKGROUND

Obesity is now recognized as a chronic disease that requires treatment to reduce its associated health risks. The increase in obesity is of concern because of the health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States. See, McGinnis M, Foege W H., "*Actual Causes of Death in the United States*," JAMA, 270, 2207 12 (1993).

It is believed that 5-10% reduction of body weight can substantially improve metabolic values, such as blood glucose, blood pressure, and lipid concentrations.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "*The New Era of Drug Treatment. Pharmacologic Treatment of Obesity: Symposium Overview*," Obes. Res., 3(suppl 4), (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

Because of the side effects expressed and the development of addiction resulting from the use of these psychoactive substances, an effective and safe medicine of central effect is still not available. Thus, there still exists a need for a more effective and safe therapeutic treatment for reducing or preventing obesity and related metabolic disorders.

In addition to obesity, there also exists an unmet need for treatment of substance addiction.

Tobacco addiction represents the most important preventable cause of illness and death in our society, responsible for thousands of deaths each year. Half of all smokers will die of diseases directly related to tobacco use, and many smokers will suffer significant morbidity. Approximately 15 million smokers try to quit, but only one million of those succeed in smoking cessation each year.

Cigarette smoke contains a large number of very complex substances the most important of which is nicotine, this being the substance to which cigarette smokers develop an addiction. Several pharmacotherapies have proven effective for the treatment of tobacco addiction. These include nicotine replacement therapies in the form of gum, patch, nasal spray and inhaler. Non-nicotine pharmacologic therapies have been developed as a method of treating nicotine addiction. Possible reagents include nicotine blockade therapy, drugs affecting serotonergic neurotransmission, anti-depressants, anxiolytics, clonidine and airway sensory replacement (Rose, 1996; and Cinciripini et al., 1998 Oncology 12: 249-256). Nicotine blockade therapy (also referred to as nicotine receptor antagonists) utilizes compounds that occupy nicotine receptors, thereby attenuating the reward received from tobacco usage (Clarke, 1991 Br. J. Addict. 86: 501-505). However, there is a need for more effective treatment for tobacco addiction.

The cannabinoid receptors are a class of cell membrane receptors under the G protein-coupled receptor superfamily. Cannabinoid receptors are activated by three major groups of ligands, (a) endocannabinoids (produced by the mammalian body), (b) plant cannabinoids (such as THC, produced by the cannabis plant) and (c) synthetic cannabinoids (such as HU-210, first synthesized in 1988 from (1R,5S)-Myrtenol). These cannabinoids exert their effects by binding to cannabinoid receptors located in the cell membrane. Endocannabinoids have been implicated in a wide variety of physiological and pathophysiological processes. To date, most drugs used to interact with the endocannabinoid system are derived from cannabis. Cannabis has received the most popularity as a raw material for products such as marijuana and hashish and its regular use can result in the development of dependence.

Two cannabinoid receptors have been characterized: cannabinoid receptor 1 (CB1), a central receptor found in the mammalian brain and peripheral tissues and cannabinoid receptor 2 (CB2), a peripheral receptor found only in the peripheral tissues. The CB1 receptor is mainly expressed in several brain areas including the limbic system (amygdala, hippocampus), hypothalamus, cerebral cortex, cerebellum, and basal ganglia. Compounds that are agonists or antagonists for one or both of these receptors have been shown to provide a variety of pharmacological effects. See, for example, Pertwee, R. G., *Pharmacology of cannabinoid CB1 and CB2 receptors*, Pharmacol. Ther., (1997) 74:129-180 and Di Marzo, V., Melck, D., Bisogno, T., DePetrocellis, L., *Endocannabinoids: endogenous cannabinoid receptor ligands with neuromodulatory action*, Trends Neurosci. (1998) 21:521-528.

The therapeutic effect of an extremely diluted (or ultra-low) form of antibodies potentized by homeopathic technology (activated potentiated form) has been discovered by the inventor of the present patent application, Dr. Oleg I. Epshtein. U.S. Pat. No. 7,582,294 discloses a medicament for treating Benign Prostatic Hyperplasia or prostatitis by administration of a homeopathically activated form of antibodies to prostate specific antigen (PSA).

The S-100 protein is an acidic cytoplasmic protein expressed in the nervous system. It has been suggested that the S-100 protein has a role in anxiety. See Ackermann et al., *S100A1-deficient male mice exhibit increased exploratory activity and reduced anxiety-related response*, Biochim. Biophys. Acta. 2006, 63(11):1307-19; Diehl et al., *Long lasting sex-specific effects upon behavior and S100b levels after maternal separation and exposure to a model of post-traumatic stress disorder in rats*, Brain Res., 2007, 144:107-16, all of which are incorporated herein by reference.

Ultra-low doses of antibodies to S-100 protein have been shown to have anxiolytic, anti-asthenic, anti-aggressive, stress-protective, anti-hypoxic, anti-ischemic, neuroprotective and nootropic activity. See Castagne V. et al., *Antibodies to S100 proteins have anxiolytic-like activity at ultra-low doses in the adult rat*, J. Pharm. Pharmacol. 2008, 60(3):309-

16; Epshtein O. I., *Antibodies to calcium-binding S100B protein block the conditioning of long-term sensitization in the terrestrial snail*, Pharmacol. Biochem. Behav., 2009, 94(1): 37-42; Voronina T. A. et al., Chapter 8. *Antibodies to S-100 protein in anxiety-depressive disorders in experimental and clinical conditions*. In "*Animal models in biological psychiatry*", Ed. Kaluéff A. V. N-Y, "Nova Science Publishers, Inc.", 2006, pp. 137-152, all of which are incorporated herein by reference.

There is a continuing need for new drug products with desired therapeutic efficacy for treatment of excess body mass or obesity and substance addiction.

SUMMARY

In one aspect, the invention provides a pharmaceutical composition comprising an activated-potentiated form of an antibody to human cannabinoid receptor. Preferably, the human cannabinoid receptor is cannabinoid receptor 1 (CB1). It is contemplated that the activated-potentiated form of an antibody of this aspect of the invention is to the entire human cannabinoid receptor 1. Specific sequences provided in the detailed description of the invention are specifically contemplated. It is contemplated that the activated-potentiated form of an antibody is to a polypeptide fragment of the human cannabinoid receptor 1. Preferably, the activated-potentiated form of an antibody is in the form of a mixture of C12, C30, and C200 homeopathic dilutions. In the particularly preferred variant, the activated-potentiated form of an antibody is in the form of a mixture of C12, C30, and C200 homeopathic dilutions impregnated onto a solid carrier. It is contemplated that the activated-potentiated form of an antibody to a human cannabinoid-receptor is a monoclonal, polyclonal or natural antibody. Preferably, the activated-potentiated form of an antibody to a human cannabinoid receptor is a polyclonal antibody. The antibody to human cannabinoid receptor may be prepared by successive centesimal dilutions coupled with shaking of every dilution.

In another aspect, the invention provides a method of treating obesity and related metabolic disorders, said method comprising administering the pharmaceutical composition of any variant or embodiment of the pharmaceutical composition aspect of the invention. The pharmaceutical composition may be administered to a patient as one or two unit dosage forms from once daily to four times daily. Twice daily administration is specifically contemplated.

In another aspect, the invention provides a method of nicotine addiction, said method comprising administering the pharmaceutical composition of any variant or embodiment of the pharmaceutical composition aspect of the invention. The pharmaceutical composition may be administered to a patient as one or two unit dosage forms from once daily to four times daily. Twice daily administration is specifically contemplated.

In another aspect, the invention provides a method of altering anthropometric parameters of a mammal expected to benefit from such alteration, said method comprising administering the pharmaceutical composition of any variant or embodiment of the pharmaceutical composition aspect of the invention. In one embodiment, the anthropometric parameter is waist circumference. In one embodiment, the anthropometric parameter is waist-height ratio. In another embodiment, the anthropometric parameter is waist-to-hip ratio. Various variants are provided.

In another aspect, the invention provides method of reducing body mass of a mammal, said method comprising administering the pharmaceutical composition of any variant or embodiment of the pharmaceutical composition aspect of the invention. In one variant, the body mass is reduced by at least 5%. In another variant, the body mass is reduced by at least 10%. body mass is reduced by at least 15%. In another variant, the body mass is reduced by less than 15%.

In another aspect, the invention provides a method of reducing body mass growth of a mammal, said method comprising administering the pharmaceutical composition of any variant or embodiment of the pharmaceutical composition aspect of the invention. In one variant, the body mass growth is reduced by at least 10%. In another variant, the body mass growth is reduced by at least 30%.

In another aspect, the invention provides a method of facilitating a reduction of food consumption in a mammal expected to benefit from such reduction, said method comprising administering the pharmaceutical composition of any variant or embodiment of the pharmaceutical composition aspect of the invention.

In another aspect, the invention provides a pharmaceutical composition comprising an activated-potentiated form of an antibody to human cannabinoid receptor and an activated-potentiated form of an antibody to S-100 protein. In one variant, the antibody to the S-100 protein is an antibody to the entire S-100 protein. Sequences for S-100 protein are provided in the specification. Preferably, the antibody to the S-100 protein is in the form of mixture of C12, C30, and C200 homeopathic dilutions impregnated onto the solid carrier. The pharmaceutical composition of this aspect of the invention may contain antibody to S-100 protein which is a monoclonal, polyclonal or natural antibody. Preferably, the antibody to the S-100 protein is a polyclonal antibody. The antibody to the S-100 protein may be prepared by successive centesimal dilutions coupled with shaking of every dilution.

In another aspect, the invention provides a method of treating a patient suffering from a psychoactive substance addiction, said method comprising administering the pharmaceutical composition comprising an activated-potentiated form of an antibody to human cannabinoid receptor and an activated-potentiated form of an antibody to S-100 protein. Preferably, the psychoactive substance is nicotine. Preferably. the administration of said combination leads to a statistically significant improvement in the ability to tolerate the quitting of smoking as measured by analysis of data of the MPSS test. Preferably, the administration of said combination leads to a statistically significant reduction of smoking of in patients with moderate nicotine addiction as measured by the Fagerström Test for Nicotine Dependence Test. Preferably, the administration of said combination leads to a statistically significant reduction of smoking of in patients with heavy nicotine addiction as measured by the Fagerström Test for Nicotine Dependence Test.

In another aspect, the invention provides a pharmaceutical composition for use in treating a patient suffering from a psychoactive substance addiction, said composition having been obtained by providing a) a potentiated solution of an antibody to human cannabinoid receptor, and b) a potentiated solution of an activated-potentiated form of an antibody to S-100 protein, each prepared by consecutive repeated dilution and multiple vertical shaking of each obtained solution in accordance with homeopathic technology, and then either combining the potentiated solutions by mixing them, or, alternatively, impregnating a carrier mass with said combined solution or with the solutions separately.

In another aspect, the invention provides pharmaceutical composition for use in treating obesity and related metabolic disorders, said composition having been obtained by providing a potentiated solution of an antibody to human cannabinoid receptor, prepared by consecutive repeated dilution and multiple vertical shaking of each obtained solution in accordance with homeopathic technology, and then optionally impregnating a carrier mass with said solution.

DETAILED DESCRIPTION

Figure 1:
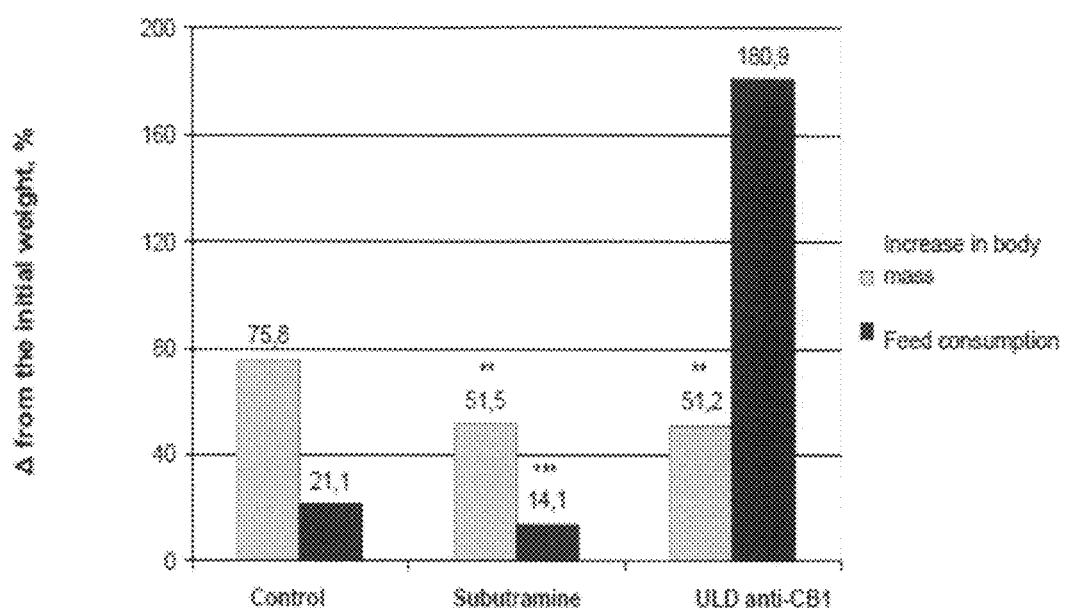
FIG. 1—Shows the effect of ULD anti-CB1 and subutramine on growth in body mass and feed consumption.

The invention is defined with reference to the appended claims. With respect to the claims, the glossary that follows provides the relevant definitions.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies."

The term "activated-potentiated form" or "potentiated form" respectively, with respect to antibodies recited herein is used to denote a product of homeopathic potentization of any initial solution of antibodies. "Homeopathic potentization" denotes the use of methods of homeopathy to impart homeopathic potency to an initial solution of relevant substance. Although not so limited, 'homeopathic potentization" may involve, for example, repeated consecutive dilutions combined with external treatment, particularly (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted $100^{12}$, $100^{30}$ and $100^{200}$ times, respectively, which is equivalent to centesimal homeopathic dilutions C12, C30 and C200. Examples of homeopathic potentization are described in U.S. Pat. Nos. 7,572,441 and 7,582,294, which are incorporated herein by reference in their entirety and for the purpose stated. While the term "activated-potentiated form" is used in the claims, the term "ultra-low doses" is used in the examples. The term "ultra-low doses" became a term of art in the field of art created by study and use of homeopathically diluted and potentized form of substance. The term "ultra-low dose" or "ultra-low doses" is meant as fully supportive and primarily synonymous with the term 'activated-potentiated" form used in the claims.

In other words, an antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. And third, the biological activity exhibited by the "activated potentiated" form of the antibody cannot be explained by the presence of the molecular form of the antibody in the final product of the homeopathic process.

For example, the activated potentiated form of antibodies may be prepared by subjecting an initial, isolated antibody in a molecular form to consecutive multiple dilutions coupled with an external impact, such as mechanical shaking. The external treatment in the course of concentration reduction may also be accomplished, for example, by exposure to ultrasonic, electromagnetic, or other physical factors. V. Schwabe "Homeopathic medicines", M., 1967, U.S. Pat. Nos. 7,229,648 to Dreyer and 4,911,897 to Alphonse, which are incorporated by reference in their entirety and for the purpose stated, describe such processes that are well accepted methods of homeopathic potentiation in the homeopathic art. This procedure gives rise to a uniform decrease in molecular concentration of the initial molecular form of the antibody. This procedure is repeated until the desired homeopathic potency is obtained. For the individual antibody, the required homeopathic potency can be determined by subjecting the intermediate dilutions to biological testing in the desired pharmacological model. Although not so limited, 'homeopathic potentization" may involve, for example, repeated consecutive dilutions combined with external treatment, particularly (mechanical) shaking. In other words, an initial solution of antibody is subjected to consecutive repeated dilution and multiple vertical shaking of each obtained solution in accordance with homeopathic technology. The preferred concentration of the initial solution of antibody in the solvent, preferably, water or a water-ethyl alcohol mixture, ranges from about 0.5 to about 5.0 mg/ml. The preferred procedure for preparing each component, i.e. antibody solution, is the use of the mixture of three aqueous or aqueous-alcohol dilutions of the primary matrix solution (mother tincture) of antibodies diluted 10012, 10030 and 100200 times, respectively, which is equivalent to centesimal homeopathic dilutions C12, C30 and C200 or the mixture of three aqueous or aqueous-alcohol dilutions of the primary matrix solution (mother tincture) of antibodies diluted 10012, 10030 and 10050 times, respectively, which is equivalent to centesimal homeopathic dilutions C12, C30 and C50. Examples of how to obtain the desired potency are also provided, for example, in U.S. Pat. Nos. 7,229,648 to Dreyer and 4,911,897 to Alphonse, which are incorporated by reference for the purpose stated. The procedure applicable to the "activated potentiated" form of the antibodies described herein is described in more detail below.

There has been a considerable amount of controversy regarding homeopathic treatment of human subjects. While the present invention relies on accepted homeopathic processes to obtain the "activated-potentiated" form of antibodies, it does not rely solely on homeopathy in human subjects for evidence of activity. It has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. The "activated-potentiated" form of the antibody provided herein are tested for biological activity in well accepted pharmacological models of activity, either in appropriate in vitro experiments, or in vivo in suitable animal models. The experiments provided further below provide evidence of biological activity in such models. The human clinical studies, also provided herein below, inter alia provide evidence that the activity observed in the animal model is well translated to human therapy. The human study also provide evidence of availability of the "activated potentiated" forms described herein to treat specified human diseases or disorders well accepted as pathological conditions in the medical science.

Also, the claimed "activated-potentiated" form of antibody encompass only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid form in which the concentration of the molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the molecular form of the antibody is below the Avogadro number. In the pharmacology of molecular forms of therapeutic substances, it is common practice to create a dose-response curve in which the level of pharmacological response is plotted against the concentration of the active drug administered to the subject or tested in vitro. The minimal level of the drug which produces any detectable response is known as a threshold dose. It is specifically contemplated and preferred that the "activated-potentiated" form of the antibodies contains molecular antibody, if any, at a concentration below the threshold dose for the molecular form of the antibody in the given biological model.

The term "CB1 receptor" has its general meaning in the art, and may include naturally occurring CB1 receptor and variants and modified forms thereof. The CB1 receptor can be from any source, but typically is mammalian.

The term "obesity" denotes a range of weight that is greater than what is generally considered healthy for a given height. Obesity ranges are determined by using weight and height to calculate a number called the "body mass index" (BMI). An adult who has a BMI between 25 and 29.9 is considered overweight. An adult who has a BMI of 30 or higher is considered obese. BMI formula as follows:

Weight÷(Height in inches)2×703=BMI

BMI does not always accurately indicate the degree of fatness. An increasing number of papers indicate that the degree of central fat (central obesity) distribution may be more closely tied to metabolic risks than BMI. It appears that measurement of the degree of central fat distribution appears to be important for the early detection of subsequent health risks, even among individuals of normal weight. S D Hsieh, H Yoshinaga and T Muto, International Journal of Obesity (2003) 27, 610-616. See also, Price G M, Uauy R, Breeze E, Bulpitt C J, Fletcher A E (August 2006). "*Weight, shape, and mortality risk in older persons: elevated waist-hip ratio, not high body mass index, is associated with a greater risk of death*" Am. J. Clin. Nutr. 84 (2): 449-60. Waist circumference and waist circumference-derived indices such as waist-to-hip ratio and waist-to-height ratio have been used as proxy measures of central obesity. Sung et. al., *Waist circumference and waist-to-height ratio of Hong Kong Chinese children*, BMC Public Health 2008, 8:324. Thus, measurement of anthropometric parameters, for example, waist circumference, waist-to-hip ratio and waist-to-height ratio, is believed to be an indicator of degree of fatness.

The term "waist-to-hip ratio" is the ratio of the circumference of the waist to that of the hips. The waist-hip ratio equals the waist circumference divided by the hip circumference. A waist-to-hip ratio of greater than 0.9 in women, and 1.0 in men, is associated with an increased risk for cardiovascular disease, and is an indication for treatment of obesity. Ideally, women should have a waist-to-hip ratio of 0.8 or less and men should have a waist-to-hip ratio of 0.95 or less.

The term "waist-to-height ratio" of a person is defined as the person's waist circumference, divided by the person's height. For people under 40, a waist-to-height ratio of over 0.5 is critical; for people in the age group between 40 and 50 the critical value is between 0.5 and 0.6, and for people over 50 the critical values start at 0.6.

The term "obesity-related metabolic disorders" refers to chronic diseases that require treatment to reduce the excessive health risks associated with obesity and exemplary disorders include type 2 diabetes mellitus, cardiovascular disorders and hypertension, hyperlipidaemia and fibrinolytic abnormalities.

The term "Fagerström test" refers to a standard test for nicotine dependence which is a test for assessing the intensity of nicotine addiction. See Heatherton, T. F., Kozlowski, L. T., Frecker, R. C., Fagerström, K. O. The Fagerström test for Nicotine Dependence: A revision of the Fagerström Tolerance Questionnaire. Br J Addict 1991; 86:1119-27. The test consists of a brief, self-report survey that measures nicotine dependence on a scale of 0-10, with 10 being the highest level of dependence.

The term "Mood and Physical Symptoms Scale" (MPSS) refers to a scale developed in the early 1980s used to assess cigarette withdrawal symptoms. (West R, Hajek P: Evaluation of the mood and physical symptoms scale (MPSS) to assess cigarette withdrawal. *Psychopharmacology* 2004, 177 (1-2):195-199). The core elements of MPSS involve 5-point rating of depressed mood, irritability, restlessness, difficulty concentrating and hunger and 6-point rating of strength of urges to smoke and time spent with these urges.

The term "Hospital Anxiety and Depression Scale" (HADS) refers to a subjective scale for screening of signs of anxiety and depression in in-patients and out-patients. See Zigmond, A. S., Snaith, R. P., *The Hospital Anxiety and Depression scale*, Acta Psychiatr. Scand., 1983, Vol. 67, pages 361-370.

The present invention provides a pharmaceutical composition for administration to a patient in need thereof, the pharmaceutical composition comprising an activated-potentiated form of an antibody to human cannabinoid receptor.

The present invention further provides a pharmaceutical composition for administration to a patient in need thereof, the pharmaceutical composition comprising an activated-potentiated form of an antibody to human cannabinoid receptor and b) an activated-potentiated form of an antibody to protein S-100.

The pharmaceutical composition in accordance with this aspect of the invention may be in the liquid form or in solid form. Each of the activated potentiated forms of the antibodies included in the pharmaceutical composition is prepared from an initial molecular form of the antibody via a process accepted in homeopathic art. The starting antibodies may be monoclonal, or polyclonal antibodies prepared in accordance with known processes, for example, as described in *Immunotechniques*, G. Frimel, M., "Meditsyna", 1987, p. 9-33; "Hum. Antibodies. *Monoclonal and recombinant antibodies, 30 years after*" by Laffly E., Sodoyer R.—2005—Vol. 14.—N 1-2, pages 33-55, both incorporated herein by reference.

It is contemplated that the pharmaceutical combination for treating obesity and nicotine addiction is administered in the amount of 6-8 tablets per day. In one variant, the mode of administration includes 2 tablets, 3 times per day. In another variant, the mode of administration includes 3 tablets, 2 times per day. In another variant, the mode of administration includes 4 tablets, 2 times per day. In another variant, the mode of administration includes 1 tablets, 6 times per day. In another variant, the mode of administration includes 2 tablets, 4 times per day.

Monoclonal antibodies may be obtained, e.g., by means of hybridoma technology. The initial stage of the process includes immunization based on the principles already developed in the course of polyclonal antisera preparation. Further stages of work involve production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen, either human cannabinoid receptor or protein S-100. The animals' immune system generates corresponding antibodies, which are collected from the animals in a known manner. This procedure enables preparation of a monospecific antibody-rich serum.

If desired, the serum containing antibodies may be purified, e.g., using affine chromatography, fractionation by salt precipitation, or ion-exchange chromatography. The resulting purified, antibody-enriched serum may be used as a starting material for the preparation of the activated-potentiated form of the antibodies. The preferred concentration of the resulting initial solution of antibody in the solvent, preferably water or water-ethyl alcohol mixture, ranges from about 0.5 to about 5.0 mg/ml.

The preferred procedure for preparing the activated-potentiated form of antibodies of the present invention or the combination antibodies according to the present invention, is the use of the mixture of three aqueous-alcohol dilutions of the primary matrix solution of antibodies diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In a preferred embodiment, the starting material for the preparation of the activated potentiated form that comprise the invention is polyclonal, animal-raised antibody to the corresponding antigen, namely, human cannabinoid receptor and/or protein S-100.

To obtain the activated-potentiated form of polyclonal antibodies to human cannabinoid receptor, the desired antigen may be injected as immunogen into a laboratory animal, preferably rabbits. In order to obtain polyclonal antibodies to human cannabinoid receptor, it is possible to use the entire molecule of human cannabinoid receptor. The following sequence (SEQ. ID. NO:1) of the human cannabinoid receptor is specifically contemplated as suitable antigen:

```
SEQ. ID. NO: 1 HUMAN CB1 RECEPTOR
Met Lys Ser Ile Leu Asp Gly Leu Ala Asp Thr Thr Phe Arg Thr
1               5                   10                  15

Ile Thr Thr Asp Leu Leu Tyr Val Gly Ser Asn Asp Ile Gln Tyr
16              20                  25                  30

Glu Asp Ile Lys Gly Asp Met Ala Ser Lys Leu Gly Tyr Phe Pro
31              35                  40                  45

Gln Lys Phe Pro Leu Thr Ser Phe Arg Gly Ser Pro Phe Gln Glu
46              50                  55                  60

Lys Met Thr Ala Gly Asp Asn Pro Gln Leu Val Pro Ala Asp Gln
61              65                  70                  75

Val Asn Ile Thr Glu Phe Tyr Asn Lys Ser Leu Ser Ser Phe Lys
76              80                  85                  90

Glu Asn Glu Glu Asn Ile Gln Cys Gly Glu Asn Phe Met Asp Ile
91              95                  100                 105

Glu Cys Phe Met Val Leu Asn Pro Ser Gln Gln Leu Ala Ile Ala
106             110                 115                 120

Val Leu Ser Leu Thr Leu Gly Thr Phe Thr Val Leu Glu Asn Leu
121             125                 130                 135

Leu Val Leu Cys Val Ile Leu His Ser Arg Ser Leu Arg Cys Arg
136             140                 145                 150

Pro Ser Tyr His Phe Ile Gly Ser Leu Ala Val Ala Asp Leu Leu
151             155                 160                 165

Gly Ser Val Ile Phe Val Tyr Ser Phe Ile Asp Phe His Val Phe
166             170                 175                 180
```

-continued

```
His Arg Lys Asp Ser Arg Asn Val Phe Leu Phe Lys Leu Gly Gly
181             185             190             195

Val Thr Ala Ser Phe Thr Ala Ser Val Gly Ser Leu Phe Leu Thr
196             200             205             210

Ala Ile Asp Arg Tyr Ile Ser Ile His Arg Pro Leu Ala Tyr Lys
211             215             220             225

Arg Ile Val Thr Arg Pro Lys Ala Val Ala Phe Cys Leu Met
226             230             235             240

Trp Thr Ile Ala Ile Val Ile Ala Val Leu Pro Leu Leu Gly Trp
241             245             250             255

Asn Cys Glu Lys Leu Gln Ser Val Cys Ser Asp Ile Phe Pro His
256             260             265             270

Ile Asp Glu Thr Tyr Leu Met Phe Trp Ile Gly Val Thr Ser Val
271             275             280             285

Leu Leu Leu Phe Ile Val Tyr Ala Tyr Met Tyr Ile Leu Trp Lys
286             290             295             300

Ala His Ser His Ala Val Arg Met Ile Gln Arg Gly Thr Gln Lys
301             305             310             315

Ser Ile Ile Ile His Thr Ser Glu Asp Gly Lys Val Gln Val Thr
316             320             325             330

Arg Pro Asp Gln Ala Arg Met Asp Ile Arg Leu Ala Lys Thr Leu
331             335             340             345

Val Leu Ile Leu Val Val Leu Ile Ile Cys Trp Gly Pro Leu Leu
346             350             355             360

Ala Ile Met Val Tyr Asp Val Phe Gly Lys Met Asn Lys Leu Ile
361             360             370             375

Lys Thr Val Phe Ala Phe Cys Ser Met Leu Cys Leu Leu Asn Ser
376             375             385             390

Thr Val Asn Pro Ile Ile Tyr Ala Leu Arg Ser Lys Asp Leu Arg
391             395             400             405

His Ala Phe Arg Ser Met Phe Pro Ser Cys Glu Gly Thr Ala Gln
406             410             415             420

Pro Leu Asp Asn Ser Met Gly Asp Ser Asp Cys Leu His Lys His
421             425             430             435

Ala Asn Asn Ala Ala Ser Val His Arg Ala Ala Glu Ser Cys Ile
436             440             445             450

Lys Ser Thr Val Lys Ile Ala Lys Val Thr Met Ser Val Ser Thr
451             455             460             465

Asp Thr Ser Ala Glu Ala Leu
466             470     472

SEQ ID NO: 2 HUMAN CB2 RECEPTOR
Met Glu Glu Cys Trp Val Thr Glu Ile Ala Asn Gly Ser Lys Asp
  1             5              10              15

Gly Leu Asp Ser Asn Pro Met Lys Asp Tyr Met Ile Leu Ser Gly
 16             20              25              30

Pro Gln Lys Thr Ala Val Ala Val Leu Cys Thr Leu Leu Gly Leu
 31             35              40              45

Leu Ser Ala Leu Glu Asn Val Ala Val Leu Tyr Leu Ile Leu Ser
 46             50              55              60

Ser His Gln Leu Arg Arg Lys Pro Ser Tyr Leu Phe Ile Gly Ser
 61             65              70              75

Leu Ala Gly Ala Asp Phe Leu Ala Ser Val Val Phe Ala Cys Ser
 76             80              85              90

Phe Val Asn Phe His Val Phe His Gly Val Asp Ser Lys Ala Val
 91             95             100             105
```

```
Phe Leu Leu Lys Ile Gly Ser Val Thr Met Thr Phe Thr Ala Ser
106                 110                 115                 120

Val Gly Ser Leu Leu Leu Thr Ala Ile Asp Arg Tyr Leu Cys Leu
121                 125                 130                 135

Arg Tyr Pro Pro Ser Tyr Lys Ala Leu Leu Thr Arg Gly Arg Ala
136                 140                 145                 150

Leu Val Thr Leu Gly Ile Met Trp Val Leu Ser Ala Leu Val Ser
151                 155                 160                 165

Tyr Leu Pro Leu Met Gly Trp Thr Cys Cys Pro Arg Pro Cys Ser
166                 170                 175                 180

Glu Leu Phe Pro Leu Ile Pro Asn Asp Tyr Leu Leu Ser Trp Leu
181                 185                 190                 195

Leu Phe Ile Ala Phe Leu Phe Ser Gly Ile Ile Tyr Thr Tyr Gly
196                 200                 205                 210

His Val Leu Trp Lys Ala His Gln His Val Ala Ser Leu Ser Gly
211                 215                 220                 225

His Gln Asp Arg Gln Val Pro Gly Met Ala Arg Met Arg Leu Asp
226                 230                 235                 240

Val Arg Leu Ala Lys Thr Leu Gly Leu Val Leu Ala Val Leu Leu
241                 245                 250                 255

Ile Cys Trp Phe Pro Val Leu Ala Leu Met Ala His Ser Leu Ala
256                 260                 265                 270

Thr Thr Leu Ser Asp Gln Val Lys Lys Ala Phe Ala Phe Cys Ser
271                 275                 280                 285

Met Leu Cys Leu Ile Asn Ser Met Val Asn Pro Val Ile Tyr Ala
286                 290                 295                 300

Leu Arg Ser Gly Glu Ile Arg Ser Ser Ala His His Cys Leu Ala
301                 305                 310                 315

His Trp Lys Lys Cys Val Arg Gly Leu Gly Ser Glu Ala Lys Glu
316                 320                 325                 330

Glu Ala Pro Arg Ser Ser Val Thr Glu Thr Glu Ala Asp Gly Lys
331                 335                 340                 345

Ile Thr Pro Trp Pro Asp Ser Arg Asp Leu Asp Leu Ser Asp Cys
346                 350                 355                 360
```

Preferably, a polypeptide fragment of human cannabinoid receptor is used as immunogen (antigen) for rabbits' immunization. In order to obtain polyclonal antibodies to obtain a polypeptide fragment of human cannabinoid receptor, it is possible to use a synthetic peptide of human cannabinoid receptor as immunogen (antigen). Suitable sequences (human CB1 receptor) for such antigen are as follows:

```
SEQ ID NO: 3.
                              Gln Arg Gly Thr Gln Lys
                              310                 315

Ser Ile Ile Ile
316         319

SEQ ID NO: 4.
        Glu Lys Leu Gln Ser Val Cys Ser Asp Ile Phe Pro His
        258     260                 265                 270

Ile Asp Glu Thr Tyr Leu
271             275 276

SEQ ID NO: 5.
                          Ile Gln Arg Gly Thr Gln Lys
                          309 310                 315

Ser Ile Ile Ile His Thr Ser Glu Asp Gly Lys Val Gln Val Thr
316                 320                 325                 330
```

```
Arg Pro Asp Gln Ala Arg Met
331             335     337

SEQ ID NO: 6.
                                                        Lys
                                                        300

Ala His Ser His Ala Val Arg Met Ile Gln Arg Gly Thr Gln Lys
301             305             310             315

Ser Ile Ile Ile His Thr Ser Glu Asp Gly Lys Val Gln Val Thr
316             320             325             330

Arg Pro Asp Gln Ala Arg Met Asp Ile Arg Leu Ala Lys Thr
331             335             340             344

SEQ ID NO: 7.
                                        Met Ser Val Ser Thr
                                        461             465

Asp Thr Ser Ala Glu Ala Leu
466             470     472

SEQ ID NO: 8.
                Thr Glu Phe Tyr Asn Lys Ser Leu Ser Ser Phe Lys
                    79  80              85                  90

Glu Asn Glu Glu Asn Ile Gln Cys Gly Glu Asn Phe Met Asp Ile
91              95              100             105

Glu Cys Phe Met Val Leu Asn Pro Ser
106             110             114

SEQ ID NO: 9.
                                                        Gln
                                                        420

Pro Leu Asp Asn Ser Met Gly Asp Ser Asp Cys Leu His Lys His
421             425             430             435

Ala Asn 436 437

SEQ ID NO: 10.
                                        Gly Thr Gln Lys
                                        312             315

Ser Ile Ile Ile His Thr Ser Glu Asp Gly
316             320             325

SEQ ID NO: 11.
    Met Thr Ala Gly Asp Asn Pro Gln Leu Val Pro Ala Asp Gln
        62              65              70              75

Val Asn Ile Thr Glu Phe Tyr Asn Lys Ser Leu Ser Ser Phe Lys
76              80              85                  90

Glu Asn Glu Glu Asn Ile Gln Cys Gly Glu Asn Phe Met Asp Ile
91              95              100             105

Glu Cys Phe Met Val Leu Asn
106             110     112

SEQ ID NO: 12.
                            Val Val Ala Phe Cys Leu Met
                            234 235              240

Trp Thr Ile Ala Ile Val Ile
241             245     247

SEQ ID NO: 13.
                        Glu Phe Tyr Asn Lys Ser Leu Ser Ser Phe Lys
                            80              85                  90

Glu Asn Glu Glu Asn Ile Gln Cys Gly Glu Asn Phe Met Asp Ile
91              95              100             105

Glu Cys Phe Met Val Leu Asn Pro Ser Gln Gln Leu Ala Ile Ala
106             110             115             120
```

-continued

```
Val Leu Ser Leu Thr Leu
121         125 126

SEQ ID NO: 14.
Asn Glu Glu Asn Ile Gln Cys Gly Glu
 92      95          100

SEQ ID NO: 15.
                        Gly Ser Pro Phe Gln Glu
                         55              60

Lys Met Thr Ala Gly Asp Asn Pro Gln Leu Val Pro Ala Asp Gln
 61          65              70                  75

Val Asn Ile Thr Glu Phe Tyr Asn Lys Ser Leu
 76          80              85  86

SEQ ID NO: 16
                                        Ala Tyr Lys
                                        223     225

Arg Ile Val Thr Arg Pro Lys Ala Val Val Ala Phe Cys Leu Met
226          230             235                 240

Trp Thr Ile Ala Ile Val Ile Ala Val Leu Pro Leu Leu Gly Trp
241          245             250                 255

Asn
256
```

The exemplary procedure for preparation of the starting polyclonal antibodies to human cannabinoid receptor may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections.

To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about −40° C. On the following day, the clot on the spatula is removed, and the remaining liquid is centrifuged for 10 minutes at 13,000 rotations per minute. Supernatant fluid is the target antiserum. The obtained antiserum is typically yellow. 20% of $NaN_3$ (weight concentration) is added in the antiserum to the final concentration of 0.02% and stored before use in frozen state at the temperature of −20° C. or without $NaN_3$ at the temperature of −70° C. To separate the target antibodies to cannabinoid receptor from the antiserum, the following solid phase absorption sequence is suitable:

10 ml of the antiserum of rabbits is diluted twofold with 0.15 M NaCl, after which 6.26 g $Na_2SO_4$ is added, mixed and incubated for 12-16 hours at 4° C. The sediment is removed by centrifugation, diluted in 10 ml of phosphate buffer and dialyzed against the same buffer during one night at room temperature. After the sediment is removed, the solution is applied to a DEAE-cellulose column balanced by phosphate buffer. The antibody fraction is determined by measuring the optical density of the eluate at 280 nm.

The isolated crude antibodies are purified using the affine chromatography method by attaching the obtained antibodies to cannabinoid receptor located on the insoluble matrix of the chromatography media, with subsequent elution by concentrated aqueous salt solutions.

The resulting buffer solution is used as the initial solution for the homeopathic dilution process used to prepare the activated potentiated form of the antibodies. The preferred concentration of the initial matrix solution of the antigen-purified polyclonal rabbit antibodies to cannabinoid receptor is 0.5-5.0 mg/ml, preferably, 2.0-3.0 mg/ml.

The brain-specific S100 protein, expressed by neurons and glial cells (astrocytes and oligodendrocytes), directly or through interactions with other proteins executes in the CNS a number of functions directed at maintaining normal brain functioning, including affecting learning and memory processes, growth and viability of neurons, regulation of metabolic processes in neuronal tissues and others. To obtain polyclonal antibodies to brain-specific protein S-100, brain-specific protein S-100 is used, which physical and chemical properties are described in the article of M. V. Starostin, S. M. Sviridov, Neurospecific Protein S-100, *Progress of Modern Biology*, 1977, Vol. 5, P. 170-178; found in the book M. B. Shtark, *Brain-Specific Protein Antigens and Functions of Neuron*, "Medicine", 1985; P. 12-14. Brain-specific protein S-100 is allocated from brain tissue of the bull by the following technique:

the bull brain tissue frozen in liquid nitrogen is converted into powder using a specialized mill;
proteins are extracted in the ratio of 1:3 (weight/volume) using an extracting buffer with homogenization;
the homogenate is heated for 10 min at 60° C. and then cooled to 4° C. in an ice bath;
thermolabile proteins are removed by centrifugation;
ammonium sulfate fractionation is carried out in stages, with subsequent removal of precipitated proteins;
the fraction containing S-100 protein is precipitated using 100% saturated ammonium sulfate accomplished by pH drop to 4.0; the desired fraction is collected by centrifugation;
the precipitate is dissolved in a minimum buffer volume containing EDTA and mercaptoethanol, the precipitate is dialyzed with deionized water and lyophilized;
fractionation of acidic proteins is followed by chromatography in ion-exchanging media, DEAE-cellulose DE-52 and then DEAE-sephadex A-50;

the collected and dialyzed fractions, which contain S-100 protein, are divided according to molecular weight by gel filtration on sephadex G-100;

purified S-100 protein is dialyzed and lyophilized.

The molecular weight of the purified brain-specific protein S-100 is 21000 D.

Owing to the high concentration of asparaginic and glutaminic acids brain-specific protein S-100 is highly acidic and occupies extreme anode position during electroendosmosis in a discontinuous buffer system of polyacrylamide gel which facilitates its identification.

The polyclonal antibodies to S-100 protein may also be obtained by a similar methodology to the methodology described for cannabinoid receptor antibodies using an adjuvant. The entire molecule of S-100 protein may be used as immunogen (antigen) for rabbits' immunization:

```
SEQ ID NO: 17 - Bovine S100B
Met Ser Glu Leu Glu Lys Ala Val Val Ala Leu Ile Asp Val Phe
1               5                   10                  15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45

Glu Glu Ile Lys Glu Gln Glu Val Val Asp Lys Val Met Glu Thr
46              50                  55                  60

Leu Asp Ser Asp Gly Asp Gly Glu Cys Asp Phe Gln Glu Phe Net
61              65                  70                  75

Ala Phe Val Ala Net Ile Thr Thr Ala Cys His Glu Phe Phe Glu
76              80                  85                  90

His Glu
91  92

SEQ ID 18 - Human S100B
Met Ser Glu Leu Glu Lys Ala Met Val Ala Leu Ile Asp Val Phe
1               5                   10                  15

His Gln Tyr Ser Gly Arg Glu Gly Asp Lys His Lys Leu Lys Lys
16              20                  25                  30

Ser Glu Leu Lys Glu Leu Ile Asn Asn Glu Leu Ser His Phe Leu
31              35                  40                  45

Glu Glu Ile Lys Glu Gln Glu Val Val Asp Lys Val Met Glu Thr
46              50                  55                  60

Leu Asp Asn Asp Gly Asp Gly Glu Cys Asp Phe Gln Glu Phe Met
61              65                  70                  75

Ala Phe Val Ala Met Val Thr Thr Ala Cys His Glu Phe Phe Glu
76              80                  85                  90

His Glu
91  92

SEQ ID NO: 19 - Human S100A1
Met Gly Ser Glu Leu Glu Thr Ala Met Glu Thr Leu Ile Asn Val
1               5                   10                  15

Phe His Ala His Ser Gly Lys Glu Gly Asp Lys Tyr Lys Leu Ser
16              20                  25                  30

Lys Lys Glu Leu Lys Glu Leu Leu Gln Thr Glu Leu Ser Gly Phe
31              35                  40                  45

Leu Asp Ala Gln Lys Asp Val Asp Ala Val Asp Lys Val Met Lys
46              50                  55                  60

Glu Leu Asp Glu Asn Gly Asp Gly Glu Val Asp Phe Gln Glu Tyr
61              65                  70                  75

Val Val Leu Val Ala Ala Leu Thr Val Ala Cys Asn Asn Phe Phe
76              80                  85                  90

Trp Glu Asn Ser
91          94

SEQ ID NO 20 - Bovine S100A1
Met Gly Ser Glu Leu Glu Thr Ala Met Glu Thr Leu Ile Asn Val
1               5                   10                  15
```

-continued

```
Phe His Ala His Ser Gly Lys Glu Gly Asp Lys Tyr Lys Leu Ser
 16          20              25                      30

Lys Lys Glu Leu Lys Glu Leu Leu Gln Thr Glu Leu Ser Gly Phe
 31          35              40                      45

Leu Asp Ala Gln Lys Asp Ala Asp Ala Val Asp Lys Val Met Lys
 46          50              55                      60

Glu Leu Asp Glu Asn Gly Asp Gly Glu Val Asp Phe Gln Glu Tyr
 61          65              70                      75

Val Val Leu Val Ala Ala Leu Thr Val Ala Cys Asn Asn Phe Phe
 76          80              85                      90

Trp Glu Asn Ser
 91          94
```

To obtain antiserum, brain-specific S-100 protein or the mixture of S-100 protein s (antigens) in complex with methylated bull seralbumin as the carrying agent with full Freund's adjuvant is prepared and added to allocated brain-specific protein S-100 which is injected subdermally to a laboratory animal—a rabbit into area of back in quantity of 1-2 ml. On 8th, 15th day repeated immunization is made. Blood sampling is made (for example, from a vein in the ear) on the 26th and the 28th day.

The obtained antiserum titre is 1:500-1:1000, forms single precipitin band with an extract of nervous tissue but does not react with extracts of heterological bodies and forms single precipitin peak both with pure protein S-100 and with the extract of nervous tissue indicating that the antiserum obtained is monospecific.

The activated potentiated form of the antibodies of the present invention may be prepared from an initial solution by homeopathic potentization, preferably using the method of proportional concentration decrease by serial dilution of 1 part of each preceding solution (beginning with the initial solution) in 9 parts (for decimal dilution), or in 99 parts (for centesimal dilution), or in 999 parts (for millesimal dilution) of a neutral solvent, starting with a concentration of the initial solution of antibody in the solvent, preferably, water or a water-ethyl alcohol mixture, in the range from about 0.5 to about 5.0 mg/ml, coupled with external impact. Preferably, the external impact involves multiple vertical shaking (dynamization) of each dilution. Preferably, separate containers are used for each subsequent dilution up to the required potency level, or the dilution factor. This method is well-accepted in the homeopathic art. See, e.g. V. Schwabe "*Homeopathic medicines*", M., 1967, p. 14-29, incorporated herein by reference for the purpose stated.

For example, to prepare a 12-centesimal dilution (denoted C12), one part of the initial matrix solution of antibodies to human cannabinoid receptor with the concentration of 3.0 mg/ml is diluted in 99 parts of neutral aqueous or aqueous-alcohol solvent (preferably, 15%-ethyl alcohol) and then vertically shaken many times (10 and more) to create the 1st centesimal dilution (denoted as C1). The 2nd centesimal dilution (C2) is prepared from the 1st centesimal dilution C1. This procedure is repeated 11 times to prepare the 12th centesimal dilution C12. Thus, the 12th centesimal dilution C12 represents a solution obtained by 12 serial dilutions of one part of the initial matrix solution of antibodies to human cannabinoid receptor with the concentration of 3.0 mg/ml in 99 parts of a neutral solvent in different containers, which is equivalent to the centesimal homeopathic dilution C12. Similar procedures with the relevant dilution factor are performed to obtain dilutions C30 and C200. The intermediate dilutions may be tested in a desired biological model to check activity. The preferred activated potentiated forms for the antibodies comprising the invention are a mixture of C12, C30, and C200 dilutions for each activated-potentiated form. When using the mixture of various homeopathic dilutions (primarily centesimal) of the active substance as biologically active liquid component, each component of the composition (e.g., C12, C30, C200) is prepared separately according to the above-described procedure until the next-to-last dilution is obtained (e.g., until C11, C29, and C199 respectively), and then one part of each component is added in one container according to the mixture composition and mixed with the required quantity of the solvent (e.g. with 97 parts for centesimal dilution).

It is possible to use the active substance as mixture of various homeopathic dilutions, e.g. decimal and/or centesimal (D20, C30, C100 or C12, C30, C50 etc.), the efficiency of which is determined experimentally by testing the dilution in a suitable biological model, for example, in models described in the examples herein.

In course of potentiation and concentration decrease, the vertical shaking may be substituted for external exposure to ultrasound, electromagnetic fields or any similar external impact procedure accepted in the homeopathic art.

Preferably, the pharmaceutical composition of the invention may be in the form of a liquid or in the solid unit dosage form. Where the pharmaceutical composition comprises two antibodies, the liquid form of the pharmaceutical composition comprises a mixture of two antibodies, preferably, at a 1:1 ratio of the activated potentiated form of antibodies to human cannabinoid receptor and the activated potentiated form of antibodies to protein S-100. The preferred liquid carrier is water or water-ethyl alcohol mixture.

The solid unit dosage form of the pharmaceutical composition of the invention may be prepared by using impregnating a solid, pharmaceutically acceptable carrier with the mixture of the activated potentiated form aqueous or aqueous-alcohol solutions of active components. Where the pharmaceutical composition comprises two antibodies, the active components are mixed, primarily in 1:1 ratio and used in liquid dosage form. Alternatively, the carrier may be impregnated consecutively with each requisite dilution. Both orders of impregnation are acceptable.

Preferably, the pharmaceutical composition in the solid unit dosage form is prepared from granules of the pharmaceutically acceptable carrier which was previously saturated with the aqueous or aqueous-alcoholic dilutions of the activated potentiated form of antibodies. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono- oligo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc), including lubricants, disintegrants, binders and coloring agents. The preferred carriers are lactose and isomalt. The pharmaceutical dosage form may further include standard pharmaceutical excipients, for example, microcrystalline cellulose and magnesium stearate.

The example of preparation of the solid unit dosage form is set forth below. To prepare the solid oral form, 100-300 μm granules of lactose are impregnated with aqueous or aqueous-alcoholic solutions of the activated potentiated form of antibodies to human cannabinoid receptor and/or the activated potentiated form of antibodies to S-100 in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Mifflin Pilotlab" by Hüttlin GmbH) with subsequent drying via heated air flow at a temperature below 40° C. The estimated quantity of the dried granules (10 to 34 weight parts) saturated with the activated potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch-XL 400 tablet press) to form 150 to 500 mg round pills, preferably, 300 mg. After tableting, 300 mg pills are obtained that are saturated with aqueous-alcohol solution (3.0-6.0 mg/pill) of the combination of the activated-potentiated form of antibodies. Each component of the combination used to impregnate the carrier is in the form of a mixture of centesimal homeopathic dilutions, preferably, C12, C30 and C200.

While the invention is not limited to any specific theory, it is believed that the activated potentiated form of the antibodies described herein do not contain the molecular form of the antibody in an amount sufficient to have biological activity attributed to such molecular form. The biological activity of the pharmaceutical composition of the invention and the combination pharmaceutical composition of the invention is amply demonstrated in the appended examples.

The pharmaceutical composition comprising activated-potentiated form of an antibody to human cannabinoid receptor may be used for administration to patients suffering from obesity and related metabolic disorders.

As shown in the appended examples, the administration of the activated potentiated form of the antibody of the present invention results in a reduction of body mass, reduction of body mass growth, reduction of central obesity and facilitating a reduction of food consumption.

In one embodiment, the present invention provides a method of treating obesity and related metabolic disorders by administering pharmaceutical compositions comprising activated potentiated form of an antibody to human cannabinoid receptor, preferably the cannabinoid receptor 1.

In another embodiment, the present invention provides a method of facilitating a reduction of food consumption in a subject expected to benefit from such reduction, by administering a pharmaceutical composition comprising activated-potentiated form of an antibody to human cannabinoid receptor, preferably the cannabinoid receptor 1.

In an embodiment, methods for altering anthropometric parameters, e.g., waist circumference, waist-to-hip ratio and waist-to-height ratio are provided. In one embodiment, methods for reducing waist circumference of a subject are provided, wherein the method comprises administering, to a subject in need thereof, pharmaceutical compositions comprising activated potentiated form of an antibody to human cannabinoid receptor in an amount effective to reduce the waist circumference of the subject. In one embodiment the human cannabinoid receptor is human cannabinoid receptor 1. In one embodiment, the waist circumference of the subject is reduced by at least about 1%. In other embodiments, the waist circumference of the subject is reduced by at least about 1.5%, 2%, 2.5%, 3% or 3.5%, compared to the subject prior to administration of the pharmaceutical compositions comprising activated potentiated form of an antibody to human cannabinoid receptor. In one embodiment, the waist circumference of the subject is reduced by at least about 1 cm. In other embodiments, the waist circumference of the subject is reduced by at least about 2 cm, 3 cm or 4 cm compared to the subject prior to administration of the pharmaceutical compositions comprising an activated potentiated form of an antibody to human cannabinoid receptor.

In another embodiment, methods for reducing body mass of a subject are provided, wherein the method comprises administering, to a subject in need thereof, pharmaceutical compositions comprising an activated potentiated form of an antibody to human cannabinoid receptor in an amount effective to reduce body mass of the subject. In one embodiment the human cannabinoid receptor is human cannabinoid receptor 1. In one embodiment, the body mass of the subject is reduced by at least about 15%. In other embodiments, the body mass of the subject is reduced by at least about 5%, 10%, or 15% compared to the subject prior to administration of the pharmaceutical compositions comprising an activated potentiated form of an antibody to human cannabinoid receptor.

In another embodiment, methods for reducing the body mass growth of a subject are provided, wherein the method comprises administering, to a subject in need thereof, pharmaceutical compositions comprising an activated potentiated form of an antibody to human cannabinoid receptor in an amount effective to reduce body mass growth of the subject. In one embodiment the human cannabinoid receptor is human cannabinoid receptor 1. In one embodiment, the body mass growth of the subject is reduced by at least about 60%. In other embodiments, the body mass growth of the subject is reduced by at least about 10%, 25%, 30%, 50%, or 60% compared to the subject prior to administration of the pharmaceutical compositions comprising an activated potentiated form of an antibody to human cannabinoid receptor.

The pharmaceutical composition comprising an activated-potentiated form of an antibody to human cannabinoid receptor and an activated-potentiated form of an antibody to S-100 protein may be used for administration to patients suffering from dependence on psychoactive substances, preferably nicotine dependence.

Applicant surprisingly discovered that the combination of an activated-potentiated form of an antibody to human cannabinoid receptor and an activated-potentiated form of an antibody to S-100 protein is useful in the treatment of substance abuse.

In one embodiment the combination of an activated-potentiated form of an antibody to human cannabinoid receptor and an activated-potentiated form of an antibody to S-100 protein is useful in the treatment of nicotine addiction.

The administration of the pharmaceutical composition comprising an activated-potentiated form of an antibody to human cannabinoid receptor 1 and an activated-potentiated form of an antibody to S-100 protein for treatment of patients with nicotine addiction improves the life quality parameters evaluated by such criteria as depression and anxiety.

It has been demonstrated experimentally that the administration of the pharmaceutical composition comprising an activated-potentiated form of an antibody to human cannabinoid receptor 1 and an activated-potentiated form of an antibody to S-100 protein for treatment of patients with nicotine addiction improves the ability to tolerate the quitting of smoking more easily and painlessly as measured by analysis of data of the MPSS test.

It has been demonstrated experimentally that the administration of the combination to patients with non-severe nicotine addiction of >4 as measured by the Fagerström Test for Nicotine Dependence leads to a reduction of smoking of at least 23% in 4 weeks; at least 36% in 8 weeks and at least 41% in 12 weeks. It has also been demonstrated experimentally that the administration of the combination to patients with non-severe nicotine addiction leads to a statistically significant reduction in the initial average number point on the Fagerström test of at least 1.34±0.14.

It has been demonstrated experimentally that the administration of the combination to patients with severe nicotine addiction of ≥7 as measured by the Fagerström Test for Nicotine Dependence leads to a reduction of smoking of at least 11% in 4 weeks; at least 22% in 8 weeks and at least 30% in 12 weeks. It has also been demonstrated experimentally that the administration of the combination to patients with non-severe nicotine addiction leads to a statistically significant reduction in the initial average number point on the Fagerström test of at least 4.42±0.30.

In one embodiment separate administration of the two independently prepared unit dosage forms, each containing one of the activated potentiated forms of antibodies of the combination is also contemplated.

The invention is further illustrated with reference to the appended non-limiting examples.

EXAMPLES

Example 1

The effect of ultra-low doses of polyclonal rabbit antibodies to human cannabinoid receptor type 1 (ULD Anti-CB1), purified on antigen, obtained by hyper-dilution of the initial matrix solution $100^{12}$, $100^{30}$, $100^{200}$ times (mixture of centesimal homeopathic dilutions C12, C30, and C200) on functioning of the cannabinoid receptor, type 1 was tested in vitro in 2 regimes: in the agonist regime and in the antagonist regime.

Agonist Regime:

Before introduction in the wells of a plate (96 wells plate, 250 μl well volume), the cells were suspended in HBSS buffer (Invitrogen), which contained 20 mM HEPES (pH=7.4). The cells were pre-incubated for 10 minutes at room temperature together with the addition of 20 μl of ULD anti-CB1 preparation. After pre-incubation, the adenylate cyclase activator NKH477 was added. The cells were incubated for 10 minutes at 37° C. and lysed. A fluorescent acceptor (cAMF, marked D2) and a fluorescent donor (cAMF antibodies, marked by europium cryptate) were introduced in the wells.

As the basal control, the cell suspension was pre-incubated in the presence of HBSS buffer (20 μl) instead of the ULD anti-CB1. As the stimulated control, the cell suspension was pre-incubated in the presence of the reference CP 55940 agonist (20 μl) instead of ULD anti-CB1.

The functional activity (cAMF concentration) was evaluated by the homogeneous fluorescence method with time resolution (HTRF). Fluorescence intensity in the basal control was considered the background, and its value was deducted from the fluorescence intensities in the experimental data (ULD anti-CB1) and control (CP 55940):

The measured specific response of the cell to the introduction of ULD anti-CB1 was calculated according to the formula: fluorescence intensity in experiment (ULD anti-CB1)—fluorescence intensity in basal control.

The measured specific response of the cell to the introduction of the reference agonist (CP 55940) was calculated according to the formula: fluorescence intensity in the control (CP 55940)—fluorescence intensity in basal control.

The results were expressed in percentages of the specific response of the cell to the introduction of the reference agonist in the stimulated control:

Percent of response of reference agonist=((measured specific response/specific response in control to introduction of reference agonist)×100%).

Antagonist Regime:

Before introduction in the wells of a plate (96 well plate, 250 μl well volume), the cells were suspended in HBSS buffer (Invitrogen), which contained 20 mM HEPES (pH=7.4). The cells were pre-incubated for 5 minutes at room temperature together with 20 μl of ULD anti-CB1. After addition in the wells of the reference CP 55940 agonist, the cells were incubated for 10 minutes at a room temperature. Adenylate cyclase activator NKH477 was added to the wells. The cells were incubated for 10 minutes at 37° C. and lysed. The fluorescent acceptor (cAMF, marked D2) and the fluorescent donor (cAMF antibodies, marked by europium cryptate) were introduced into the wells.

As the basal control, the cell suspension was pre-incubated in the presence of the reference antagonist AM 281 (20 μl) instead of ULD anti-CB1. The reference CP 55940 agonist was not added in the wells with the basal control. As the stimulated control, the cell suspension was pre-incubated in the presence of HBSS buffer, which contained 20 mM HEPES (pH=7.4), and the reference CP 55940 agonist (20 μl).

Functional activity (cAMF concentration) was evaluated by the homogeneous fluorescence method with time resolution (HTRF). Fluorescence intensity in the basal control was taken as the background, and its value was deducted from the fluorescence intensities in the experiment (ULD anti-Cb1) and control (CP 55940):

The measured specific response of the cell to the introduction of ULD anti-CB1 was calculated according to the formula: fluorescence intensity in experiment (ULD anti-CB1)–fluorescence intensity in basal control.

The measured specific response of the cell to the introduction of the reference agonist (CP 55940) was calculated according to the formula: fluorescence intensity in control (CP 55940)–fluorescence intensity in basal control.

The results were expressed in percentages of the inhibition of specific response of the cell to the introduction of the reference agonist in the control:

Percent of inhibition of response of reference agonist=100%–((measured specific response/specific response in control to introduction of reference agonist)×100%).

As a result of the investigation, it was shown (see Table 1) that ULD anti-CB1 changes the functional activity of the cannabinoid receptor type 1 as measured by intracellular concentration of cAMF.

The test substance (ultra-low doses of antibodies to cannabinoid receptor type 1 (mixture of homeopathic dilutions C12, C30 and C200) exhibited the cannabinoid receptor type 1 agonist activity. The magnitude of the agonist effect 21% in reference to the effect of standard CP 55940 agonist (standard agonist effect is taken as 100%).

TABLE 1

| Receptor | Test substance | Content of ULD anti-CB1 in the well (volume %) (total volume in the well was 200 microliters) | Agonist regime | | Antagonist regime | | Explanation |
|---|---|---|---|---|---|---|---|
| | | | % of response to ULD anti-CB1 | Standard agonist | % inhibition of the antagonist | Standard antagonist | |
| CB1 receptor | ULD anti-CB1 | 10% | 21 | CP 55940 | 0 | AM 281 | ULD anti-CB1 possess agonist effect, the magnitude of which is 21% in reference to the effect of standard agonist |

Example 2

The test substance was in the form of an aqueous solution of ultra-low doses of polyclonal rabbit antibodies to human cannabinoid receptor type 1 (ULD anti-CB1), purified on antigen, obtained by hyper-dilution of the initial matrix solution $100^{12}$, $100^{30}$, $100^{200}$ times (mixture of centesimal homeopathic dilutions C12, C30, and C200).

40 male mice of the C57B1 line were used in the study (weight at the beginning of the study: 13.5-15.5 g). 10 mice received the regular standard feed (standard diet); 30 mice received the standard feed with high calorie additives (high calories diet) and, simultaneously, either distilled water (control, 0.4 ml/mouse) or Subutramine (Meridia 10 mg capsules, Abbott GmbH, Germany) (10 mg/Kg) or ULD anti-CB1 (0.4 ml/mouse). All preparations were given intragastrically once a day in the course of 5 months. The mice consumption of feed was measured before test substances were introduced. The mice consumption of feed was also measured each week thereafter. The consumption of feed was evaluated as an average quantity of food (in grams), consumed by a mouse after 1 and 2 months of the study, and as an average quantity of feed per 10 g of mouse body mass.

Over the entire period of observation, the mice on the low calorie diet consumed, on average, 15% less feed than mice on the high calorie diet (Table 2). Both Subutramine and ULD anti-CB1 decreased the consumption of feed. The effect of Subutramine was expressed somewhat higher: the consumption of feed decreased in a week by 19.3% ($p<0.05$), while ULD anti-CB1 decreased the consumption of feed by 9.3% in reference to the control ($p>0.05$). Table 2 shows the results of the study, specifically, the effect of ULD anti-CB1 and Subutramine on feed consumption of C57B1 mice (average values over 5 months of observation), M±m.

TABLE 2

| Preparation | Consumption of feed (g/mouse) per day | Consumption of feed (g per 10 g of body mass) per day |
|---|---|---|
| Standard diet | 2.95 ± 1.42 | 1.35 ± 0.05 |
| High calorie diet + distilled water | 3.4 ± 1.64# | 1.54 ± 0.05# |
| High calorie diet + Subutramine | 2.75 ± 1.36** | 1.28 ± 0.05** |
| High calorie diet + ULD anti-CB1 | 3.10 ± 2.02 | 1.44 ± 0.08 |

\*\*differences from control are statistically significant with $p < 0.01$;
\#differences from standard diet are statistically significant with $p < 0.05$.

On the twentieth week of the experiment, mice on the high fat diet that received ULD anti-CB1 consumed more feed in comparison with the first week of the experiment, which is shown in FIG. 1. FIG. 1 shows the effect of ULD anti-CB1 and Subutramine on the growth of C57B1 mice body mass and consumption of food per 10 g of weight after the last $20^{th}$ week of the experiment.

A reduction of body mass growth of 51.2% was observed in mice that received ULD anti-CB1 compared to the control. Subutramine on the last twentieth week of the experiment lowered body mass by 51.5% in comparison with the control group.

Example 3

The test substance was in the form of an aqueous solution of ultra-low doses of polyclonal rabbit antibodies to human cannabinoid receptor type 1 (ULD anti-CB1), purified on antigen, obtained by hyper-dilution of the initial matrix solution $100^{12}$, $100^{30}$, $100^{200}$ times (mixture of centesimal homeopathic dilutions C12, C30, and C200).

33 male mice of the C57B1 line were used in the study (weight at the beginning of the study: 13.09±0.738 g). The mice received the modified diet with high (45%) fat content and simultaneously either distilled water (control, 0.2 ml/mouse) or Subutramine (10 mg/Kg) or ULD anti-CB1 (0.2 ml/mouse). All ULD anti-CB1 preparations were given intragastrically once a day in the course of 2 months. The mice weight was measured on Philips Cucina HR 239016 (Hungary) electronic scales until beginning to introduce the preparations (initially) and also each week after beginning to introduce them. The body mass growth of the mice was evaluated as a percentage of the initial weight.

Beginning 6 weeks from the introduction, ULD anti-CB1 lowered the body mass growth of the mice that were maintained on the high fat diet. Table 3 depicts the average weekly mass (grams) of the C57B 16 mice that received the high fat diet and ULD anti-CB1 (0.2 ml/mouse) or Subutramine (10 mg/Kg) (M±m). Table 3 shows the body mass growth of the mice.

TABLE 3

| Group | Body mass (grams), weeks of study | | | | | | | | |
|---|---|---|---|---|---|---|---|---|---|
| | 0 | 1 | 2 | 3 | 4 | 5 | 6 | 7 | 8 |
| Distilled water | 12.18 ± 0.501 | 15.27 ± 0.982 | 15.27 ± 0.488 | 16.00 ± 0.972 | 18.18 ± 0.569 | 17.27 ± 0.557 | 20.18 ± 0.501 | 20.55 ± 0.608 | 21.45 ± 0.857 |

TABLE 3-continued

| Group | Body mass (grams), weeks of study | | | | | | | | |
|---|---|---|---|---|---|---|---|---|---|
| | 0 | 1 | 2 | 3 | 4 | 5 | 6 | 7 | 8 |
| Δ to initial | | 25.4 | 25.4 | 31.3 | 49.3 | 41.8 | 65.7 | 68.7 | 76.1 |
| Subutramine | 13.82 ± 1.094 | 13.45 ± 0.474 | 16.73 ± 0.407 * | 19.82 ± 0.501 ** | 20.18 ± 0.784 | 20.91 ± 0.563 ** | 22.36 ± 0.927 | 23.64 ± 1.343 | 22.91 ± 1.091 |
| Δ to initial | | −2.6 | 21.1 | 43.4 | 46.1 | 51.3 | 61.8 | 71.1 | 65.8 |
| ULD anti-CB1 | 13.27 ± 0.619 | 16.18 ± 0.182 | 17.45 ± 0.282 ** | 19.64 ± 0.453 ** | 20.18 ± 0.423 * | 20.18 ± 0.423 ** | 19.82 ± 0.501 | 21.64 ± 0.364 | 22.00 ± 0.467 |
| Δ to initial | | 21.9 | 31.4 | 47.9 | 52.1 | 52.1 | 49.43 | 63.0 | 65.8 |

Note:
* p < 0.05 compared to the control group;
** p < 0.001 compared to the control group As shown, ULD anti-CB1 lowers the body mass growth of mice on the high fat diet, decreasing food consumption and it is not inferior in efficacy to the known, widely used compound for reduction of body mass, subutramine.

Example 4

300 mg tablets saturated with a water-alcohol solution (6 mg/tablet) of the activated-potentiated form of polyclonal rabbit antibodies to human cannabinoid receptor type 1, purified on antigen, in ultra-low dose, obtained by hyper-dilution of the initial matrix solution $100^{12}$, $100^{30}$, $100^{200}$ times (mixture of centesimal homeopathic dilutions C12, C30, and C200 (ULD anti-CB1).

80 subjects participated in the study (20 men and 60 women) from 20 to 69 years of age (average age was 40.2±1.26 years), 68.7% of whom suffered from excess body mass or obesity (grade I-III). The subjects were given 1 tablet, 2 times a day. Table 4 depicts the demographic and anthropometric indicators of the patients included in the study. Data of all the subjects who participated in the study (n=80) were included in the safety analysis. During the entire subject-observation period, a good tolerance of the preparation was noted. Adverse effects were absent. All subjects of the groups being studied completed the treatment in the time limits established by the study protocol; no patients dropped out early. During evaluation of the effect of ULD anti-CB1 on change in the body mass of the subjects, it was revealed that use of the preparation led to a reduction in the body mass of 56 (70%) patients. In 24 (30%) patients, the weight remained unchanged or insignificantly increased. However, it should be noted that among such patients, 14 (17.5%) initially had normal body mass (BMI<25 Kg/m$^2$).

TABLE 4

| Parameter | | Value | |
|---|---|---|---|
| Age (years) | M ± m | 40.2 ± 1.26 | |
| Height (centimeters) | M ± m | 167.1 ± 0.89 | |
| Weight (kg) | M ± m | 80.3 ± 1.85 | |
| Sex | male | 20 persons (25%) | |
| | female | 60 persons (75%) | |
| BMI, kg/m$^2$ | M ± m | 28.7 ± 0.6 | |
| BMI, kg/m$^2$ | Less than 25 | 25 persons (31.3%) | Normal body mass |
| | 25-29.99 | 28 persons (35%) | Excess body mass (pre-obesity) |
| | 30-34.99 | 20 persons (25%) | Obesity of I degree |
| | 35-39.99 | 5 persons (6.2%) | Obesity II degree |
| | 40 or more | 2 persons (2.5%) | Obesity III degree |

Figure 2:
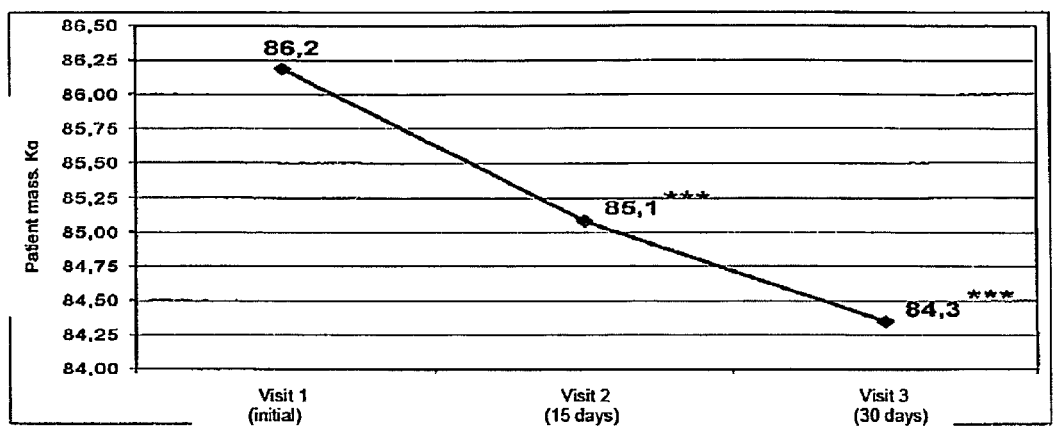
FIG. 2—Shows the reduction in body mass after administration of ULD anti-CB1.

With respect to the patients who responded to the therapy, a statistically significant decrease in body mass (p<0.001) was observed. After only 15 days of administration of ULD anti-CB1, the reduction in body mass was 1.1 Kg (1.3%) and in 1 month it reached 1.9 Kg (2.2%) of the original value (FIG. 2).

With respect to the patients who responded to the therapy, a statistically significant (p<0.001) decrease in the circumference of the waist and thighs was observed only one (1) week after the beginning of administration of ULD anti-CB1, which at the end of the therapy reached 2.3% and 2.7%, respectively. Table 5 presents the dynamics of the change in the circumference of the waist and thighs.

TABLE 5

| | Day 1 (initial) | Day 7 | Day 14 | Day 15 | Day 16 | Day 22 | Day 29 | Day 30 |
|---|---|---|---|---|---|---|---|---|
| | circumference of waist, cm | | | | | | | |
| M ± m, cm | 96.3 ± 1.97 | 95.2 ± 2.07 ** | 93.7 ± 1.82 *** | 94.2 ± 1.96 *** | 95.1 ± 2.16 *** | 94.5 ± 2.16 *** | 94.3 ± 2.10 *** | 94.1 ± 2.07 *** |
| Δ from initial, % | | −1.1% | −2.7% | −2.2% | −1.2% | −1.9% | −2.1% | −2.3% |
| | circumference of thighs, cm | | | | | | | |
| M ± m, cm | 110.8 ± 1.52 | 110.8 ± 1.66 *** | 109.3 ± 1.37 ** | 109.9 ± 1.50 *** | 108.7 ± 1.60 *** | 108.3 ± 1.56 *** | 108.1 ± 1.58 *** | 107.8 ± 1.69 *** |
| Δ from initial, % | | 0.0% | −1.4% | −0.8% | −1.9% | −2.3% | −2.4% | −2.7% |

** p < 0.01 in reference to the initial value;
*** p < 0.001 in reference to the initial value In evaluation of patients' feeling of hunger on the visual analog scale (VAS), the greatest intensity of feeling of hunger was noted in the evening hours. At the end of 1 month after the beginning of administration of ULD anti-CB1, the level of hunger in the evening hours was significantly reduced (with $p<0.001$) from 49.4±3.75 to 42.0±4.32 points. There was also a noted tendency in the morning and daytime to reduced feelings of hunger (from 20.5±3.23 to 13.6±1.78 points in the morning hours, from 44.7±3.45 to 27.3±3.72 points in the daytime). Although the data related to morning hunger did not reach statistically significant values at the end of the therapy, which observation could be related to the moderate initial values, the dynamics could not be ignored.

Thus, the clinical study of ULD anti-CB1, which were carried out, confirmed the high tolerance of the test preparation; there were no adverse effects upon taking the test preparation.

Example 5

Fagerström Test for Nicotine Dependence

This example provides the test itself. The relevant data are provided separately further herein below. The Fagerström test for nicotine dependence is a test for assessing the intensity of nicotine addiction. See Heatherton, T. F., Kozlowski, L. T., Frecker, R. C., Fagerström, K. O. The Fagerström test for Nicotine Dependence: A revision of the Fagerström Tolerance Questionnaire. Br J Addict 1991; 86:1119-27, incorporated herein by reference. In the studies described further herein below, the patients answered all questions. The total score gives the degree of nicotine dependence. The degree of nicotine dependence is evaluated by the sum of the scores as follows: less than 4—weak dependence; 4-6—average degree of dependence; and 7-10—strong dependence

TABLE 6

1. How soon after waking up do you smoke your first cigarette?

| | |
|---|---|
| More than 60 minutes | 0 |
| 31-60 minutes | 1 |
| 6-30 minutes | 2 |
| Less than 5 minutes | 3 |

2. Is it difficult for you not to smoke in places where smoking is prohibited, for example, at meetings, on an airplane, at the movies, etc.?

| | |
|---|---|
| No | 0 |
| Yes | 1 |

3. What cigarette is hardest for you to give up?

| | |
|---|---|
| First in the morning | 1 |
| From any other | 0 |

4. How many cigarettes do you smoke a day?

| | |
|---|---|
| 10 or less | 0 |
| 11-20 | 1 |
| 21-30 | 2 |
| 31 or more | 3 |

5. Do you smoke more the first hours of the morning than at any other time of the day?

| | |
|---|---|
| No | 0 |
| Yes | 1 |

6. Do you smoke even if you are sick and have to stay in bed most of the day?

| | |
|---|---|
| No | 0 |
| Yes | 1 |

Example 6

Mood and Physical Symptoms Scale Test (MPSS)

This example provides the test itself. The relevant data are provided separately further herein below. In the studies described herein below, the patients who have given up smoking answered 12 questions (the score was assessed from 1 to 5 points for each question), evaluating feelings during the last 24 hours (questions 1-7), attraction to smoking (questions 8-9) and expression of physical symptoms (questions 10-12). The patients circled only one number for each question. The summary of the results can be divided into three domains (M—questions 1-7, C—questions 8-9 and P—questions 10-12) or by the overall score, which can vary from the minimum (12 points) to the maximum (60 points), reflecting the level of nicotine withdrawal symptoms.

TABLE 7

Please indicate for each question how you have felt during the last 24 hours (Circle only one number for each question)

| | Was not | To slight degree | Rather strong | Very strong | Extremely strong |
|---|---|---|---|---|---|
| 1. Depressed | 1 | 2 | 3 | 4 | 5 |
| 2. Anxious | 1 | 2 | 3 | 4 | 5 |
| 3. Irritated | 1 | 2 | 3 | 4 | 5 |
| 4. Worried | 1 | 2 | 3 | 4 | 5 |
| 5. Feeling of hunger | 1 | 2 | 3 | 4 | 5 |
| 6. Poor attention | 1 | 2 | 3 | 4 | 5 |
| 7. Sleep disorder | 1 | 2 | 3 | 4 | 5 |

8. For how long did you feel like smoking in the last 24 hours? (Circle only one number)

| Not once | Not very long | Lesser part of day | Most of day | Almost always | Constantly |
|---|---|---|---|---|---|
| 0 | 1 | 2 | 3 | 4 | 5 |

9. How strong was the desire to smoke? (Circle only one number)

| None | Slight | Moderate | Strong | Very strong | Extremely strong |
|---|---|---|---|---|---|
| 0 | 1 | 2 | 3 | 4 | 5 |

Were there any manifestations in the last 24 hours? (Circle only one number)

| | No | Slight | Moderate | Strong | Very strong |
|---|---|---|---|---|---|
| 10. Mouth pains | 1 | 2 | 3 | 4 | 5 |
| 11. Constipation | 1 | 2 | 3 | 4 | 5 |
| 12. Cough/pain in throat | 1 | 2 | 3 | 4 | 5 |

West, R., Hajek, P. Evaluation of the mood and physical symptoms scale (MPSS) to assess cigarette withdrawal. Psychopharmacology, 2004; Volume 177, Numbers 1-2, 195-199, incorporated herein by reference.

Example 7

Hospital Anxiety and Depression Scale (HADS)

This example provides the test itself. The relevant data are provided separately further herein below. Hospital Anxiety and Depression Scale (HADS) is a subjective scale and for screening of signs of anxiety and depression in hospital in-patients and out-patients. See Zigmond, A. S., Snaith, R. P. The Hospital Anxiety and Depression scale//Acta Psychiatr. Scand.—1983.—Vol. 67.—P. 361-370, incorporated herein by reference.

Application method: The scale form is given to the patient to fill out and is accompanied by the following instructions:

"Scientists believe that emotions play an important role in the outset of most illnesses. If your doctor knows more about your experiences, he can better help you. This questionnaire is designed to help your doctor understand how you feel. Do not pay attention to the numbers and letters on the left part of the questionnaire. Carefully read each statement and in the empty space on the left, put an "X" next to the answer that best corresponds to how you have felt the last week. Do not think too much about each statement. Your first reaction will always be the best."

The scale includes 14 statements divided into 2 subscales: "anxiety" (odd-numbered questions—1, 3, 5, 7, 9, 11, 13) and "depression" (even-numbered questions—2, 4, 6, 8, 10, 12, 14). Each statement has 4 possible answers, reflecting the magnitude of the feeling or emotion and incrementally characterizing the seriousness of the symptom from 0 (absence) to 3 (maximum).

In interpreting the results, the overall indicator for each subscale is taken into account, divided into 3 ranges of values: 0-7 indicating "normal" (absence of reliably expressed symptoms of anxiety and depression); 8-10 indicating "subclinical anxiety/depression"; and 11 and above indicating "clinical anxiety/depression."

TABLE 8

| | |
|---|---|
| 1 I experience tension, I am not myself | |
| always | 3 |
| often | 2 |
| from time to time, sometimes | 1 |
| do not at all experience | 0 |
| 2 What gave me great satisfaction before still gives me the same feeling | |
| definitely so | 0 |
| probably so | 1 |
| only so to a small degree | 2 |
| not at all so | 3 |
| 3 I feel afraid as if something bad is about to happen | |
| definitely so, and the fear is very strong | 3 |
| yes, that is so, but the fear is not very strong | 2 |
| sometimes, but it does not worry me | 1 |
| do not at all experience | 0 |
| 4 I am able to laugh and see something funny in this or that event | |
| definitely so | 0 |
| probably so | 1 |
| only so to a small degree | 2 |
| not at all able | 3 |
| 5 Disquieting thoughts run through my mind | |
| constantly | 3 |
| most of the time | 2 |
| from time to time | 1 |
| only sometimes | 0 |
| 6 I am in good spirits | |
| not at all | 3 |
| very rarely | 2 |
| sometimes | 1 |
| practically always | 0 |
| 7 It is easy for me to sit down and relax | |
| definitely so | 0 |
| probably so | 1 |
| only rarely so | 2 |
| cannot at all | 3 |
| 8 It seems to me that I have begun to do everything slowly | |
| practically always | 3 |
| often | 2 |
| sometimes | 1 |
| not at all | 0 |
| 9 I experience inner tension or trembling | |
| do not at all experience | 0 |
| sometimes | 1 |
| often | 2 |
| very often | 3 |

TABLE 8-continued

| | |
|---|---|
| 10 I do not look after my appearance | |
| definitely so | 3 |
| I do not spend as much time on it as I should | 2 |
| perhaps, I have begun to pay less attention to it | 1 |
| I look after myself the same as before | 0 |
| 11 I experience restlessness, as if I constantly have to move | |
| definitely so | 3 |
| probably so | 2 |
| only so to a small degree | 1 |
| do not at all experience | 0 |
| 12 I feel that my affairs (pursuits, interests) can bring me a sense of satisfaction | |
| the same as usual | 0 |
| yes, but not to the degree as before | 1 |
| significantly less than usual | 2 |
| do not at all feel so | 3 |
| 13 I have sudden feelings of panic | |
| very often | 3 |
| rather often | 2 |
| not so often | 1 |
| does not at all happen | 0 |
| 14 I can receive satisfaction from a good book, radio or television program | |
| often | 0 |
| sometimes | 1 |
| rarely | 2 |
| very rarely | 3 |

Zigmond, A. S., Snaith, R. P. The Hospital Anxiety and Depression scale // Acta Psychiatr. Scand. - 1983. - Vol. 67. - P. 361-370, incorporated herein by reference.

Example 8

Comparative, double-blind, placebo-controlled clinical study, to evaluate the combination of ultra-low dose of antibodies to S-100 protein and ultra-low doses of antibodies to CB1 receptor, and ultra-low doses of antibodies to CB1 receptor for treatment of moderate nicotine dependence and obesity.

300 mg tablets saturated with water-alcohol solutions (6 mg/tab) of ultra-low doses of polyclonal rabbit antibodies to brain-specific protein S-100 (ULD anti-S100) and to cannabinoid receptor type 1 (ULD anti-CB1), each obtained by hyper-dilution of the initial matrix solution $100^{12}$, $100^{30}$, $100^{200}$ times (mixture of centesimal homeopathic dilutions C12, C30, and C200) were used in the study (ULD anti-S100+ULD anti-CB1). Also, 300 mg tablets saturated with a water-alcohol solution (6 mg/tab) of ultra-low doses of polyclonal rabbit antibodies to cannabinoid receptor type 1 (ULD anti-CB1) obtained by hyper-dilution of the initial matrix solution $100^{12}$, $100^{30}$, $100^{200}$ times (mixture of centesimal homeopathic dilutions C12, C30, and C200) were used in the study.

59 patients having the desire to quit smoking were included in a comparative, double-blind, placebo-controlled study, evaluating the efficacy of the ULD anti-S100+ULD anti-CB1 combination and anti-CB1 in treating nicotine dependence. 22 patients were included in the active preparation group and were given ULD anti-S100+ULD anti-CB1, 1 tablet 3 times a day. 17 patients were included in the comparison preparation group and were given ULD anti-Cb1, 1 tablet 3 times a day. 20 patients were included in the placebo group and were given 1 tablet 3 times a day (a tablet of granulated lactose and excipients without any active ingredients). The therapy lasted 12 weeks. All three groups of patients were comparable in the initial demographic, anthropometric, and clinical laboratory indicators. All patients had nicotine dependence of minor degree according to the Fagerström test (less than 4 points), smoked not less than one year, and had degree one (1) obesity (body mass index [BMI]=30.0-34.9 kg/m$^2$). All patients in the study completed treatment in the periods required by the study protocol; no patients dropped out early.

Analysis of the data showed that the number of patients who gave up smoking increased among patients who received ULD anti-S100+ULD anti-CB1 and ULD anti-CB1 (Table 9). In the ULD anti-S100+ULD group, the portion of patients who quit smoking in 4 weeks of treatment was 23%; in 8 weeks, 36%; and at the end of 12 weeks, it reached 41%. In the ULD anti-CB1 group, the corresponding indicators were 12%, 24% and 29% (versus 5%, 5% and 10%, respectively, in the placebo group). The difference in the efficacy of treatment in accordance to the main efficacy parameter in comparison with placebo therapy was 31% (for the ULD anti-S100+ULD group) and 19% (for the ULD anti-CB1 group), and it was statistically significant.

The evaluation of the effect of the ULD anti-S100+ULD anti-CB1 showed substantial decrease in nicotine dependence, both for the group as a whole, and for the subgroup of patients who were not able to give up smoking. The initial average total score on the Fagerström test was 2.67±0.14. In 12 weeks of treatment, it decreased to 1.33±0.14; moreover, the decrease was statistically significant, not only in comparison with the initial indicators, but also in comparison with the placebo group. Patients who received ULD anti-CB1 and who did not quit smoke also demonstrated positive dynamics with respect to manifestation of their nicotine dependence, which at the end of 3 months of therapy was significantly lower in comparison with the initial levels and with placebo.

The analysis of data of the Mood and Physical Symptoms Scale (MPSS) showed that nicotine withdrawal symptoms gradually diminished among patients who gave up smoking, reaching minimum values 12 weeks after the beginning of the treatment for both ULD anti-S100+ULD anti-CB1 and ULD anti-CB1 (Table 9). The lowest total score was recorded in ULD anti-S100+ULD anti-CB1 group, showing that the administration of the ULD anti-S100+ULD anti-CB1 and ULD anti-CB1 combination made it possible to bear the quitting of smoking more easily and painlessly, including in comparison with ULD anti-CB1 alone.

All groups of patients included in the study had patients with first degree obesity. Body Mass Index (BMI) was measured for patients in all groups in the study at regular intervals. The results of the study are presented in Table 10.

TABLE 10

Average differences between initial and current weight (in kg) on each visit

| Period | ULD anti-S100 + ULD anti-CB1 (n = 22; M ± SE) | ULD anti-CB1 (n = 17; M ± SE) | Placebo (n = 20; M ± SE) |
| --- | --- | --- | --- |
| 0 | 0 ± 0.0 | 0 ± 0.0 | 0 ± 0.0 |
| 2 weeks | −1.2 ± 0.5 | −0.9 ± 0.3 | −0.4 ± 0.2 |
| 4 weeks | −1.7 ± 0.4 | −1.5 ± 0.5 | −0.5 ± 0.4 |
| 6 weeks | −2.5 ± 0.4 | −2.2 ± 0.6 | −1.3 ± 0.4 |
| 8 weeks | −3.1 ± 0.7* | −2.8 ± 0.7* | −1.3 ± 0.4 |
| 10 weeks | −3.8 ± 0.6* | −3.4 ± 0.8* | −1.8 ± 0.5* |
| 12 weeks | −4.2 ± 0.9* | −3.8 ± 1.0* | −1.8 ± 0.6* |

Note:
For evaluation of the statistical significance of the change, the Student double-sided criteria in the Dunnett modification was used to make comparisons of weight on the control visit (visit 0) with all subsequent visits.
Significant differences ($p < 0.05$) are noted with asterisks.

Figure 3:
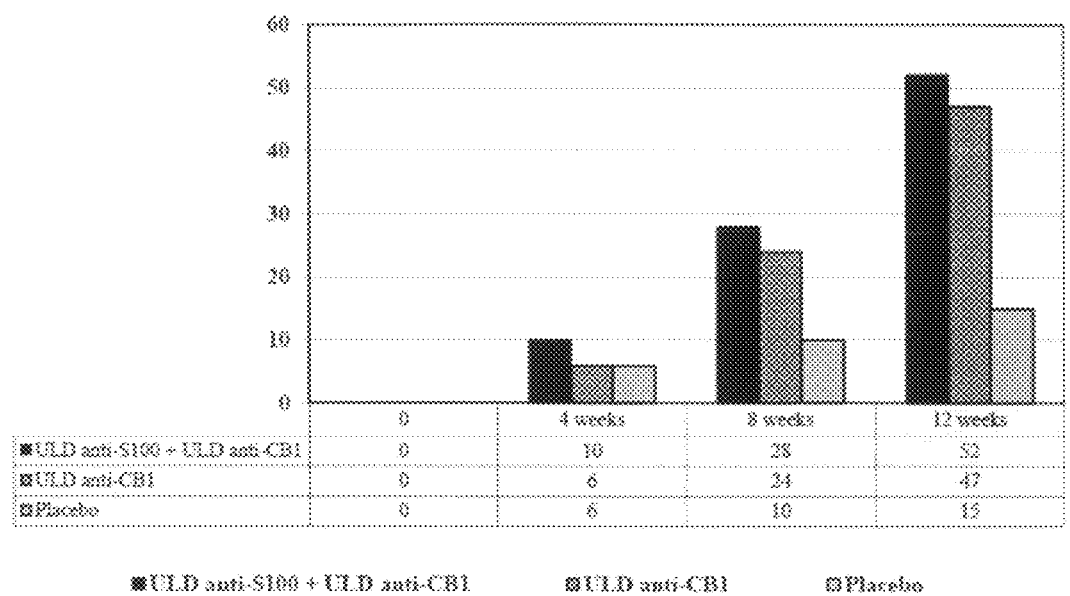
FIG. 3—Shows reduction of weight of 5% or more in patients.

As a result of the 12-week course of treatment, the body mass in both test groups significantly decreased in comparison with the placebo. In 3 months of therapy, about half of the patients (52% and 47%) in the two test groups reduced their weight by 5% or more in comparison with the initial state (in comparison with 15% of patients in the placebo group; with $p<0.05$) (FIG. 3).

Evaluation of the safety of the therapy, conducted on the basis of the record of adverse events in the period of treatment and a follow-up study of laboratory indicators, showed good tolerance to both ULD anti-S100+ULD anti-CB1 and ULD anti-CB1. The safety analysis included the data of all patients who participated in the study (n=59). No negative effect of the treatment on the central nervous system was revealed; indicators of psychiatric consequences were absent. This conclu-

TABLE 9

Dynamics of basic indicators depending on form of therapy

| Period | ULD anti-S100 + ULD anti-CB1 (M ± SE) | ULD anti-CB1 (M ± SE) | Placebos (M ± SE) |
| --- | --- | --- | --- |
| Fagerström test, points (n—number of smokers) | | | |
| Initial | 2.64 ± 0.10 (n = 22) | 2.65 ± 0.12 (n = 17) | 2.65 ± 0.11 (n = 20) |
| Initial | 2.67 ± 0.14 (n = 12) | 2.58 ± 0.14 (n = 12) | 2.66 ± 0.11 (n = 18) |
| 12 weeks | 1.33 ± 0.14* # (n = 12) | 1.25 ± 0.13* (n = 12) | 2.39 ± 0.26 (n = 18) |
| Portion of patients who quit smoking, % | | | |
| 4 weeks | 23% (n = 5) | 12% (n = 2) | 5% (n = 1) |
| 8 weeks | 36% (n = 8) | 24% (n = 4) | 5% (n = 1) |
| 12 weeks | 41% (n = 10) | 29% (n = 5) | 10% (n = 2) |
| Symptoms scale (MPSS) cancelled, points (n—number giving up smoking) | | | |
| 4 weeks | 33.4 ± 1.25 (n = 5) | 33.00 ± 2.00 (n = 2) | 36 (n = 1) |
| 8 weeks | 28.12 ± 1.02 (n = 8) | 25.50 ± 2.22 (n = 4) | 34 (n = 1) |
| 12 weeks | 14.85 ± 2.41* ** (n = 10) | 20.80 ± 1.62* (n = 5) | 32.50 ± 0.50 (n = 2) |
| Hospital Anxiety and Depression Scale (HADS), points (n—number of patients examined) | | | |
| Initial | 11.73 ± 0.36 (n = 22) | 11.41 ± 0.50 (n = 17) | 11.4 ± 0.44 (n = 20) |
| 4 weeks | 10.32 ± 0.32 (n = 22) | 10.47 ± 0.30 (n = 17) | 11.95 ± 0.45 (n = 20) |
| 8 weeks | 8.59 ± 0.33 (n = 22) | 9.88 ± 0.32 (n = 17) | 12.55 ± 0.35 (n = 20) |
| 12 weeks | 7.68 ± 0.46* # (n = 22) | 9.41 ± 0.35 (n = 17) | 12.05 ± 0.18 (n = 20) |

Note:
*statistical significance of differences with the placebo group, $p < 0.05$;
**statistical significance of differences between the ULD anti-S100 + ULD anti-CB1 and ULD anti-CB1 groups, $p < 0.05$;
statistical significance of differences with initial values sion was confirmed by monitoring of indicators using the Hospital Anxiety and Depression Scale (HADS) (Table 9). ULD anti-S100+ULD anti-CB1 demonstrated a positive effect on symptoms of anxiety and depression, which were significantly reduced toward the end of the therapy in comparison with both initial values and placebo. Adverse events were absent. The laboratory indicators, including general and biochemical analyses of the blood and clinical analysis of urine, did not show any significant deviations from normal values.

Thus, the study demonstrated the efficacy and safety of the ULD anti-S100+ULD anti-CB1 combination and ULD anti-CB1 in the treatment of nicotine dependence. The effects of the treatments were evident from the high percentages of patients who gave up smoking, the reduction in the withdrawal symptoms in the course of the therapy, and the reduction of nicotine dependence in those patients who could not quit smoking. All of the observed effects were statistically significant in comparison with the placebo group. The efficacy of the ULD anti-S100+ULD anti-CB1 combination exceeded the efficacy of ULD anti-CB1 alone. The safety profile was excellent for both ULD anti-S100+ULD anti-CB1 combination and ULD anti-CB1. Both ULD anti-S100+ULD anti-CB1 combination and ULD anti-CB1 did not lead to the appearance of clinically manifested anxiety and/or depression. Also, decrease of body mass in patients with degree 1 obesity was demonstrated.

Example 9

Comparative, double-blind, placebo-controlled clinical study, to evaluate the combination of ultra-low dose of antibodies to S-100 protein and ultra-low doses of antibodies to CB1 receptor, and ultra-low doses of antibodies to CB1 receptor for treatment of heavy nicotine dependence.

300 mg tablets saturated with water-alcohol solutions (6 mg/tab) of ultra-low doses of polyclonal rabbit antibodies to brain-specific protein S-100 (ULD anti-S100) and to cannabinoid receptor type 1 (ULD anti-CB1), each obtained by hyper-dilution of the initial matrix solution $100^{12}$, $100^{30}$, $100^{200}$ times (mixture of centesimal homeopathic dilutions C12, C30, C200) were used in the study (ULD anti-S100+ULD anti-CB1). Also, 300 mg tablets saturated with a water-alcohol solution (6 mg/tab) of ultra-low doses of polyclonal rabbit antibodies to cannabinoid receptor type 1 (ULD anti-CB1) obtained by hyper-dilution of the initial matrix solution $100^{12}$, $100^{30}$, $100^{200}$ times (mixture of centesimal homeopathic dilutions C12, C30, C200) were used in the study.

To evaluate the efficacy of ULD anti-S100+ULD anti-CB1 in treating heavy nicotine dependence, a comparative, placebo-controlled, double-blind study was carried out with the participation of 61 patients who were randomized in three groups as follows: 18 patients in the first group (ULD anti-S100+ULD anti-CB1, 1 tablet, 4 times a day), 22 patients in the second group (ULD anti-CB1, 1 tablet, 4 times a day) and 21 patients in the placebo group (1 tablet, 4 times a day) (a tablet of granulated lactose and excipients without any active ingredients). The therapy lasted 12 weeks. Patients of the three groups were comparable according to initial indicators, including demographic, physical and laboratory: According to the primary results of the Fagerström test, all participants had heavy nicotine dependence (≥7 points) and smoked more than three years. In the course of monthly visits, the patients were monitored and given physical and laboratory examinations and tests (Fagerström test, Hospital Anxiety and Depression Scale [HADS]). In patients who gave up smoking, withdrawal symptoms were measured (Mood and Physical Symptoms Scale [MPSS]). All patients completed treatment in the periods established by the study protocol; no patients dropped out early.

The results of the study are presented in Table 11:

TABLE 11

| Dynamics of basic indicators depending on form of therapy | | | |
|---|---|---|---|
| Period | ULD anti-S100 + ULD anti-CB1 (M ± SE) | ULD anti-CB1 (M ± SE) | Placebo (M ± SE) |
| Fagerström test, points (n—number of smokers) | | | |
| Initial | 8.78 ± 0.26 (n = 18) | 8.55 ± 0.26 (n = 22) | 8.52 ± 0.24 (n = 21) |
| Initial | 8.92 ± 0.34 (n = 12) | 8.47 ± 0.24 (n = 17) | 8.47 ± 0.25 (n = 20) |
| 12 weeks | 4.50 ± 0.26* ** # (n = 12) | 6.11 ± 0.26* (n = 17) | 8.73 ± 0.23 (n = 19) |
| Portion of patients who quit smoking, % | | | |
| 4 weeks | 11% (n = 2) | 9% (n = 2) | 5% (n = 1) |
| 8 weeks | 22% (n = 4) | 14% (n = 3) | 5% (n = 1) |
| 12 weeks | 30% (n = 6) | 23% (n = 5) | 10% (n = 2) |
| Withdrawal symptoms scale (MPSS), points (n—number giving up smoking) | | | |
| 4 weeks | 54.33 ± 1.2 (n = 2) | 54.50 ± 0.50 (n = 2) | 54 (n = 1) |
| 8 weeks | 46.75 ± 1.89 (n = 4) | 47.33 ± 0.67 (n = 3) | 50 (n = 1) |
| 12 weeks | 38.67 ± 0.88* ** (n = 6) | 45.22 ± 1.11* (n = 5) | 53.00 ± 1.00 (n = 2) |
| Hospital Anxiety and Depression Scale (HADS), points (n—number of patients examined) | | | |
| Initial | 12.61 ± 0.36 (n = 18) | 12.50 ± 0.29 (n = 22) | 11.81 ± 0.38 (n = 21) |
| 4 weeks | 11.17 ± 0.31 (n = 18) | 11.95 ± 0.25 (n = 22) | 13.05 ± 0.47 (n = 21) |
| 8 weeks | 9.56 ± 0.30 (n = 18) | 10.86 ± 0.22 (n = 22) | 13.24 ± 0.39 (n = 21) |
| 12 weeks | 7.72 ± 0.32* # (n = 18) | 9.50 ± 0.19 (n = 22) | 12.67 ± 0.23 (n = 21) |

Note:
*differences with the placebo group are statistically significant with $p < 0.05$;
**differences ULD anti-S100 + ULD anti-CB1 and ULD anti-CB1 groups are statistically significant with $p < 0.05$;
differences with the initial parameters are statistically significant with $p < 0.05$.

In the ULD anti-S100+ULD anti-CB1 group, the portion of patients who quit smoking in 4 weeks of treatment was 11%; in 8 weeks, 22%; and at the end of 12 weeks, it reached 30%. In the ULD anti-CB1 group, the corresponding indicators were 9%, 14% and 23% (versus 5%, 5% and 10%, respectively, in the placebo group).

Manifestations of nicotine dependence substantially decreased upon administration of ULD anti-S100+ULD anti-CB1, both for the group as a whole and for the subgroup of patients who were not able to give up smoking (see Table 11). Their initial average total points on the Fagerström test was 8.92±0.34, which in 12 weeks of treatment decreased almost twice, to 4.50±0.26. Moreover, the decrease was statistically significant not only in comparison with the initial values, but also in comparison with ULD anti-CB1 group and placebo.

Upon administration of ULD anti-S100+ULD anti-CB1 combination, the patients also exhibited statistically significant decrease in withdrawal symptoms in comparison with both ULD anti-CB1 (with $p<0.05$) and placebo ($p<0.005$) based on the data of the MPSS scale, reaching minimal values at 12 weeks after the beginning of the treatment.

The safety evaluation was also conducted. The safety analysis included data from all patients who participated in the study (n=61), and it was conducted on the basis of the record of adverse events and follow-up study of laboratory indicators. The results of the study showed not only good tolerance of ULD anti-S100+ULD anti-CB1 combination and ULD anti-CB1 alone, but also to the lack of any adverse events connected with taking the medicines. No negative effect of the treatment on the central nervous system was revealed; indicators of psychiatric consequences were absent. This conclusion was confirmed by monitoring of indicators using the Hospital Anxiety and Depression Scale (HADS) (Table 11). ULD anti-S100+ULD anti-CB1 demonstrated a positive effect on symptoms of anxiety and depression, which were significantly reduced toward the end of the therapy in comparison with both initial values and placebo. Adverse events were absent. The laboratory indicators, including general and biochemical analyses of the blood and clinical analysis of urine, did not show any significant deviations from normal values.

Thus, the results of the study demonstrated the efficacy and safety of the ULD anti-S100+ULD anti-CB1 in the treatment of heavy nicotine dependence. During the 12-week course of treatment, almost a third of the smokers were able to free themselves of their dependence on nicotine. As shown on Table 11, the efficacy of ULD anti-S100+ULD anti-CB1 exceeded the efficacy of the placebo in a statistically significant manner. ULD anti-S100+ULD anti-CB1 greatly improved patients' ability to more easily and painlessly endure smoking cessation. Among those patients who could not give up smoking in the course of observation, manifestation of nicotine dependence significantly diminished upon administration of ULD anti-S100+ULD anti-CB1 in comparison with both ULD anti-CB1 and placebo.

Both ULD anti-S100+ULD anti-CB1 and ULD anti-CB1 were characterized by excellent safety profile and absence of adverse effects on central nervous system.

Example 10

The effects of I) the combination of ultra-low doses of polyclonal rabbit antibodies to brain-specific protein S-100 (ULD anti-S100) and ultra-low doses of antibodies to cannabinoid receptor type 1 (ULD anti-CB1), each obtained by hyper-dilution of the initial matrix solution $100^{12}$, $100^{30}$, $100^{200}$ times (mixture of centesimal homeopathic dilutions C12, C30, C200) (ULD anti-S100+ULD anti-CB1), ii) ULD anti-CB1 alone, and iii) ULD anti-S100 alone, on motor activity of mice were studied to evaluate their anti-nicotine properties.

40 white outbred male mice (22-25 g, 1.5 mo.) were used. 10 mice were intact. The rest of the mice were administered nicotine subcutaneously over 4 days at the dose of 0.3 mg/kg, Nicotine administration was preceded (1 hour prior) by intragastrical administration of either distilled water (control, 0.4 ml/mouse), or ULD anti-S100 (0.4 ml/mouse), or ULD anti-CB1 (0.4 ml/mouse), or ULD anti-S100+ULD anti-CB1 (0.4 ml/mouse). 30 minutes after the last administration of nicotine, an "open field" test was conducted. The animals were placed in the center of a TruScan photo-sensory installation (Coulbourn, USA), where the vertical and horizontal locomotor activity of the animals was automatically recorded in the course of two (2) minutes. The "open field" model makes it possible to evaluate the effect of the compounds on the locomotor activity of the animals (Gershenfield H. K., Neumann P. E., Mathis C., Crawley J. N., Li X., Paul S. M. Mapping quntative Trait Loci for Open-Field Behavior in Mice. Behavioral Genetics.—1997.—Vol. 27.—No 3.—p. 201-209, which is incorporated herein by reference in its entirety and for the purpose stated). The installation parameters: size 270×270×360 mm, divided into 64 squares, 2.5× 2.5, with 25 mm openings situated in the platform floor, illumination of a 150 watt lamp.

Nicotine is an alkaloid found in plants of the Solanaceae family, predominantly in tobacco, and possessing psychotropic activity. The effect of nicotine is believed to be indirect through peripheral and central N-choline receptors. Depending on the dose, introduction of this alkaloid into the body can cause the development of anxiety-depression symptomotology, euphoria, excitation or, vice versa, calmness. Furthermore, prolonged application of nicotine leads to dependence. Preparations used to make it easier to quit smoking, among other things aim to eliminate pathologic changes in the psychoemotional sphere, which facilitates the release of patients from pathologic predilection to tobacco.

In the present study, the administration of nicotine led to an increase in the motor activity of mice: activity time increased by 8.2% ($p<0.05$), distance traveled by 5.1%, quantity of openings investigated by 78.2% ($p<0.05$), study reaction time by 76.9%, while immobility time, conversely decreased by as 13.5% ($p<0.05$) in comparison with the intact animals.

ULD anti-S100 alone did not have a significant effect in reference to the control with respect to specific parameters under investigation. ULD anti-CB1 reduced activity time and traveled distance of the mice in the test group to the level of intact mice. However, ULD anti-CB1 did not have effect on immobility period, quantity of openings and reaction period. At the same time, the combined administration of ULD anti-CB1 and ULD anti-S100 reduced activity time and, correspondingly, increased immobility time to the level of intact animals, considerably reduced traveled distance (by 29.2% in comparison with the control and by 25.5% in comparison with the intact animals) and somewhat decreased the activity (the quantity of openings dropped by 15.3%, reaction time dropped by 17.4%).

Thus, the administration of ULD anti-CB1, and combined administration of ULD anti-CB1 and ULD anti-S100, contributes to the elimination of changes in the behavior of animals caused by the administration of nicotine. Use of an ULD anti-CB1+ULD anti-S100 combination was more effective in comparison with the administration of ULD anti-CB1 alone.

TABLE 12

Effect of preparations on the motor activity of mice (open field test), M ± m

|  | Activity time, sec | Distance of motion, cm | Immobility time, sec | Quantity of openings investigated | Reaction study time |
|---|---|---|---|---|---|
| Intact | 74.1 ± 1.9 | 393.6 ± 19.6 | 46.0 ± 2.0 | 5.5 ± 1.0 | 2.6 ± 0.6 |
| Control | 80.2 ± 1.3* | 413.7 ± 15.4 | 39.8 ± 1.3* | 9.8 ± 1.4* | 4.6 ± 0.9# |
| ULD anti-S100 | 76.5 ± 1.4 | 434.4 ± 23.5 | 43.5 ± 1.4 | 10.0 ± 1.1** | 5.1 ± 1.0# |
| ULD anti-CB1 | 72.4 ± 1.4## | 366.3 ± 19.1 | 47.6 ± 1.4## | 9.8 ± 0.8 | 5.6 ± 1.1*# |
| ULD anti-CB1 + ULD anti-S100 | 74.5 ± 2.8 | 393.1 ± 28 | 45.5 ± 2.9 | 8.3 ± 1.5 | 3.8 ± 0.7 | differences from the intact are statistically significant: *with $p < 0.05$; **with $p < 0.01$
difference from the control are statistically significant: #with $p < 0.05$; ##with $p < 0.01$

---

What is claimed is:

1. A pharmaceutical composition comprising a homeopathically potentized form of an antibody to human cannabinoid receptor.

2. The pharmaceutical composition of claim 1, wherein said human cannabinoid receptor is cannabinoid receptor 1 (CB1).

3. The pharmaceutical composition of claim 2, wherein said homeopathically potentized form of an antibody is to the entire human cannabinoid receptor 1.

4. The pharmaceutical composition of claim 3, wherein said entire human cannabinoid receptor 1 consists of sequence provided in SEQ ID No: 1.

5. The pharmaceutical composition of claim 2, wherein said homeopathically potentized form of an antibody is to a polypeptide fragment of the human cannabinoid receptor 1.

6. The pharmaceutical composition of claim 5, wherein said polypeptide fragment of the human cannabinoid receptor 1 is selected from the group consisting of sequences provided in SEQ ID Nos: 3-16.

7. The pharmaceutical composition of claim 1, wherein said homeopathically potentized form of an antibody is in the form of a mixture of C12, C30, and C200 homeopathic dilutions.

8. The pharmaceutical composition of claim 1, wherein said homeopathically potentized form of an antibody is in the form of a mixture of C12, C30, and C200 homeopathic dilutions impregnated onto a solid carrier.

9. The pharmaceutical composition of claim 1, wherein the homeopathically potentized form of an antibody to a human cannabinoid-receptor is a monoclonal, polyclonal or natural antibody.

10. The pharmaceutical composition of claim 9, wherein said homeopathically potentized form of an antibody to a human cannabinoid-receptor is a polyclonal antibody.

11. The pharmaceutical composition of claim 1, wherein the antibody to human cannabinoid receptor is prepared by successive centesimal dilutions coupled with shaking of every dilution.

* * * * *

SEQUENCE LISTING

<160> NUMBER OF SEQ ID NOS: 20

<210> SEQ ID NO 1
<211> LENGTH: 472
<212> TYPE: PRT
<213> ORGANISM: Homo sapiens
<220> FEATURE:
<221> NAME/KEY: SOURCE
<222> LOCATION: 1..472
<223> OTHER INFORMATION: /mol_type="protein"
      /organism="Homo sapiens"

<400> SEQUENCE: 1

```
Met Lys Ser Ile Leu Asp Gly Leu Ala Asp Thr Thr Phe Arg Thr Ile
1               5                   10                  15

Thr Thr Asp Leu Leu Tyr Val Gly Ser Asn Asp Ile Gln Tyr Glu Asp
            20                  25                  30

Ile Lys Gly Asp Met Ala Ser Lys Leu Gly Tyr Phe Pro Gln Lys Phe
        35                  40                  45

Pro Leu Thr Ser Phe Arg Gly Ser Pro Phe Gln Glu Lys Met Thr Ala
    50                  55                  60

Gly Asp Asn Pro Gln Leu Val Pro Ala Asp Gln Val Asn Ile Thr Glu
65                  70                  75                  80

Phe Tyr Asn Lys Ser Leu Ser Ser Phe Lys Glu Asn Glu Glu Asn Ile
                85                  90                  95

Gln Cys Gly Glu Asn Phe Met Asp Ile Glu Cys Phe Met Val Leu Asn
            100                 105                 110

Pro Ser Gln Gln Leu Ala Ile Ala Val Leu Ser Leu Thr Leu Gly Thr
        115                 120                 125

Phe Thr Val Leu Glu Asn Leu Leu Val Leu Cys Val Ile Leu His Ser
    130                 135                 140

Arg Ser Leu Arg Cys Arg Pro Ser Tyr His Phe Ile Gly Ser Leu Ala
145                 150                 155                 160

Val Ala Asp Leu Leu Gly Ser Val Ile Phe Val Tyr Ser Phe Ile Asp
                165                 170                 175

Phe His Val Phe His Arg Lys Asp Ser Arg Asn Val Phe Leu Phe Lys
            180                 185                 190

Leu Gly Gly Val Thr Ala Ser Phe Thr Ala Ser Val Gly Ser Leu Phe
        195                 200                 205

Leu Thr Ala Ile Asp Arg Tyr Ile Ser Ile His Arg Pro Leu Ala Tyr
    210                 215                 220

Lys Arg Ile Val Thr Arg Pro Lys Ala Val Val Ala Phe Cys Leu Met
225                 230                 235                 240
```

-continued

```
Trp Thr Ile Ala Ile Val Ile Ala Val Leu Pro Leu Gly Trp Asn
                245                 250                 255

Cys Glu Lys Leu Gln Ser Val Cys Ser Asp Ile Phe Pro His Ile Asp
            260                 265                 270

Glu Thr Tyr Leu Met Phe Trp Ile Gly Val Thr Ser Val Leu Leu Leu
        275                 280                 285

Phe Ile Val Tyr Ala Tyr Met Tyr Ile Leu Trp Lys Ala His Ser His
290                 295                 300

Ala Val Arg Met Ile Gln Arg Gly Thr Gln Lys Ser Ile Ile Ile His
305                 310                 315                 320

Thr Ser Glu Asp Gly Lys Val Gln Val Thr Arg Pro Asp Gln Ala Arg
                325                 330                 335

Met Asp Ile Arg Leu Ala Lys Thr Leu Val Leu Ile Leu Val Val Leu
            340                 345                 350

Ile Ile Cys Trp Gly Pro Leu Leu Ala Ile Met Val Tyr Asp Val Phe
        355                 360                 365

Gly Lys Met Asn Lys Leu Ile Lys Thr Val Phe Ala Phe Cys Ser Met
370                 375                 380

Leu Cys Leu Leu Asn Ser Thr Val Asn Pro Ile Ile Tyr Ala Leu Arg
385                 390                 395                 400

Ser Lys Asp Leu Arg His Ala Phe Arg Ser Met Phe Pro Ser Cys Glu
                405                 410                 415

Gly Thr Ala Gln Pro Leu Asp Asn Ser Met Gly Asp Ser Asp Cys Leu
            420                 425                 430

His Lys His Ala Asn Asn Ala Ala Ser Val His Arg Ala Ala Glu Ser
        435                 440                 445

Cys Ile Lys Ser Thr Val Lys Ile Ala Lys Val Thr Met Ser Val Ser
        450                 455                 460

Thr Asp Thr Ser Ala Glu Ala Leu
465                 470

<210> SEQ ID NO 2
<211> LENGTH: 360
<212> TYPE: PRT
<213> ORGANISM: Homo sapiens
<220> FEATURE:
<221> NAME/KEY: SOURCE
<222> LOCATION: 1..360
<223> OTHER INFORMATION: /mol_type="protein"
      /organism="Homo sapiens"

<400> SEQUENCE: 2

Met Glu Glu Cys Trp Val Thr Glu Ile Ala Asn Gly Ser Lys Asp Gly
1               5                   10                  15

Leu Asp Ser Asn Pro Met Lys Asp Tyr Met Ile Leu Ser Gly Pro Gln
            20                  25                  30

Lys Thr Ala Val Ala Val Leu Cys Thr Leu Gly Leu Leu Ser Ala
        35                  40                  45

Leu Glu Asn Val Ala Val Leu Tyr Leu Ile Leu Ser Ser His Gln Leu
    50                  55                  60

Arg Arg Lys Pro Ser Tyr Leu Phe Ile Gly Ser Leu Ala Gly Ala Asp
65                  70                  75                  80

Phe Leu Ala Ser Val Val Phe Ala Cys Ser Phe Val Asn Phe His Val
                85                  90                  95

Phe His Gly Val Asp Ser Lys Ala Val Phe Leu Leu Lys Ile Gly Ser
            100                 105                 110
```

```
Val Thr Met Thr Phe Thr Ala Ser Val Gly Ser Leu Leu Thr Ala
        115                 120                 125

Ile Asp Arg Tyr Leu Cys Leu Arg Tyr Pro Pro Ser Tyr Lys Ala Leu
    130                 135                 140

Leu Thr Arg Gly Arg Ala Leu Val Thr Leu Gly Ile Met Trp Val Leu
145                 150                 155                 160

Ser Ala Leu Val Ser Tyr Leu Pro Leu Met Gly Trp Thr Cys Cys Pro
                165                 170                 175

Arg Pro Cys Ser Glu Leu Phe Pro Leu Ile Pro Asn Asp Tyr Leu Leu
            180                 185                 190

Ser Trp Leu Leu Phe Ile Ala Phe Leu Phe Ser Gly Ile Ile Tyr Thr
        195                 200                 205

Tyr Gly His Val Leu Trp Lys Ala His Gln His Val Ala Ser Leu Ser
    210                 215                 220

Gly His Gln Asp Arg Gln Val Pro Gly Met Ala Arg Met Arg Leu Asp
225                 230                 235                 240

Val Arg Leu Ala Lys Thr Leu Gly Leu Val Leu Ala Val Leu Leu Ile
                245                 250                 255

Cys Trp Phe Pro Val Leu Ala Leu Met Ala His Ser Leu Ala Thr Thr
            260                 265                 270

Leu Ser Asp Gln Val Lys Lys Ala Phe Ala Phe Cys Ser Met Leu Cys
        275                 280                 285

Leu Ile Asn Ser Met Val Asn Pro Val Ile Tyr Ala Leu Arg Ser Gly
    290                 295                 300

Glu Ile Arg Ser Ser Ala His His Cys Leu Ala His Trp Lys Lys Cys
305                 310                 315                 320

Val Arg Gly Leu Gly Ser Glu Ala Lys Glu Glu Ala Pro Arg Ser Ser
                325                 330                 335

Val Thr Glu Thr Glu Ala Asp Gly Lys Ile Thr Pro Trp Pro Asp Ser
            340                 345                 350

Arg Asp Leu Asp Leu Ser Asp Cys
        355                 360

<210> SEQ ID NO 3
<211> LENGTH: 19
<212> TYPE: PRT
<213> ORGANISM: Homo sapiens
<220> FEATURE:
<221> NAME/KEY: SOURCE
<222> LOCATION: 1..19
<223> OTHER INFORMATION: /mol_type="protein"
      /organism="Homo sapiens"

<400> SEQUENCE: 3

Glu Lys Leu Gln Ser Val Cys Ser Asp Ile Phe Pro His Ile Asp Glu
1               5                   10                  15

Thr Tyr Leu

<210> SEQ ID NO 4
<211> LENGTH: 10
<212> TYPE: PRT
<213> ORGANISM: Homo sapiens
<220> FEATURE:
<221> NAME/KEY: SOURCE
<222> LOCATION: 1..10
<223> OTHER INFORMATION: /mol_type="protein"
      /organism="Homo sapiens"

<400> SEQUENCE: 4
```

```
Gln Arg Gly Thr Gln Lys Ser Ile Ile Ile
1               5                   10
```

<210> SEQ ID NO 5
<211> LENGTH: 29
<212> TYPE: PRT
<213> ORGANISM: Homo sapiens
<220> FEATURE:
<221> NAME/KEY: SOURCE
<222> LOCATION: 1..29
<223> OTHER INFORMATION: /mol_type="protein"
      /organism="Homo sapiens"

<400> SEQUENCE: 5

```
Ile Gln Arg Gly Thr Gln Lys Ser Ile Ile Ile His Thr Ser Glu Asp
1               5                   10                  15
Gly Lys Val Gln Val Thr Arg Pro Asp Gln Ala Arg Met
            20                  25
```

<210> SEQ ID NO 6
<211> LENGTH: 45
<212> TYPE: PRT
<213> ORGANISM: Homo sapiens
<220> FEATURE:
<221> NAME/KEY: SOURCE
<222> LOCATION: 1..45
<223> OTHER INFORMATION: /mol_type="protein"
      /organism="Homo sapiens"

<400> SEQUENCE: 6

```
Lys Ala His Ser His Ala Val Arg Met Ile Gln Arg Gly Thr Gln Lys
1               5                   10                  15
Ser Ile Ile Ile His Thr Ser Glu Asp Gly Lys Val Gln Val Thr Arg
            20                  25                  30
Pro Asp Gln Ala Arg Met Asp Ile Arg Leu Ala Lys Thr
        35                  40                  45
```

<210> SEQ ID NO 7
<211> LENGTH: 12
<212> TYPE: PRT
<213> ORGANISM: Homo sapiens
<220> FEATURE:
<221> NAME/KEY: SOURCE
<222> LOCATION: 1..12
<223> OTHER INFORMATION: /mol_type="protein"
      /organism="Homo sapiens"

<400> SEQUENCE: 7

```
Met Ser Val Ser Thr Asp Thr Ser Ala Glu Ala Leu
1               5                   10
```

<210> SEQ ID NO 8
<211> LENGTH: 36
<212> TYPE: PRT
<213> ORGANISM: Homo sapiens
<220> FEATURE:
<221> NAME/KEY: SOURCE
<222> LOCATION: 1..36
<223> OTHER INFORMATION: /mol_type="protein"
      /organism="Homo sapiens"

<400> SEQUENCE: 8

```
Thr Glu Phe Tyr Asn Lys Ser Leu Ser Ser Phe Lys Glu Asn Glu Glu
1               5                   10                  15
Asn Ile Gln Cys Gly Glu Asn Phe Met Asp Ile Glu Cys Phe Met Val
            20                  25                  30
```

```
Leu Asn Pro Ser
        35

<210> SEQ ID NO 9
<211> LENGTH: 18
<212> TYPE: PRT
<213> ORGANISM: Homo sapiens
<220> FEATURE:
<221> NAME/KEY: SOURCE
<222> LOCATION: 1..18
<223> OTHER INFORMATION: /mol_type="protein"
      /organism="Homo sapiens"

<400> SEQUENCE: 9

Gln Pro Leu Asp Asn Ser Met Gly Asp Ser Asp Cys Leu His Lys His
1               5                   10                  15

Ala Asn

<210> SEQ ID NO 10
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"

<400> SEQUENCE: 10

Gly Thr Gln Lys Ser Ile Ile Ile His Thr Ser Glu Asp Gly
1               5                   10

<210> SEQ ID NO 11
<211> LENGTH: 51
<212> TYPE: PRT
<213> ORGANISM: Homo sapiens
<220> FEATURE:
<221> NAME/KEY: SOURCE
<222> LOCATION: 1..51
<223> OTHER INFORMATION: /mol_type="protein"
      /organism="Homo sapiens"

<400> SEQUENCE: 11

Met Thr Ala Gly Asp Asn Pro Gln Leu Val Pro Ala Asp Gln Val Asn
1               5                   10                  15

Ile Thr Glu Phe Tyr Asn Lys Ser Leu Ser Ser Phe Lys Glu Asn Glu
                20                  25                  30

Glu Asn Ile Gln Cys Gly Glu Asn Phe Met Asp Ile Glu Cys Phe Met
            35                  40                  45

Val Leu Asn
        50

<210> SEQ ID NO 12
<211> LENGTH: 14
<212> TYPE: PRT
<213> ORGANISM: Homo sapiens
<220> FEATURE:
<221> NAME/KEY: SOURCE
<222> LOCATION: 1..14
<223> OTHER INFORMATION: /mol_type="protein"
      /organism="Homo sapiens"

<400> SEQUENCE: 12

Val Val Ala Phe Cys Leu Met Trp Thr Ile Ala Ile Val Ile
1               5                   10
```

```
<210> SEQ ID NO 13
<211> LENGTH: 47
<212> TYPE: PRT
<213> ORGANISM: Homo sapiens
<220> FEATURE:
<221> NAME/KEY: SOURCE
<222> LOCATION: 1..47
<223> OTHER INFORMATION: /mol_type="protein"
      /organism="Homo sapiens"

<400> SEQUENCE: 13

Glu Phe Tyr Asn Lys Ser Leu Ser Ser Phe Lys Glu Asn Glu Glu Asn
1               5                   10                  15

Ile Gln Cys Gly Glu Asn Phe Met Asp Ile Glu Cys Phe Met Val Leu
            20                  25                  30

Asn Pro Ser Gln Gln Leu Ala Ile Ala Val Leu Ser Leu Thr Leu
        35                  40                  45

<210> SEQ ID NO 14
<211> LENGTH: 9
<212> TYPE: PRT
<213> ORGANISM: Homo sapiens
<220> FEATURE:
<221> NAME/KEY: SOURCE
<222> LOCATION: 1..9
<223> OTHER INFORMATION: /mol_type="protein"
      /organism="Homo sapiens"

<400> SEQUENCE: 14

Asn Glu Glu Asn Ile Gln Cys Gly Glu
1               5

<210> SEQ ID NO 15
<211> LENGTH: 32
<212> TYPE: PRT
<213> ORGANISM: Homo sapiens
<220> FEATURE:
<221> NAME/KEY: SOURCE
<222> LOCATION: 1..32
<223> OTHER INFORMATION: /mol_type="protein"
      /organism="Homo sapiens"

<400> SEQUENCE: 15

Gly Ser Pro Phe Gln Glu Lys Met Thr Ala Gly Asp Asn Pro Gln Leu
1               5                   10                  15

Val Pro Ala Asp Gln Val Asn Ile Thr Glu Phe Tyr Asn Lys Ser Leu
            20                  25                  30

<210> SEQ ID NO 16
<211> LENGTH: 34
<212> TYPE: PRT
<213> ORGANISM: Homo sapiens
<220> FEATURE:
<221> NAME/KEY: SOURCE
<222> LOCATION: 1..34
<223> OTHER INFORMATION: /mol_type="protein"
      /organism="Homo sapiens"

<400> SEQUENCE: 16

Ala Tyr Lys Arg Ile Val Thr Arg Pro Lys Ala Val Val Ala Phe Cys
1               5                   10                  15

Leu Met Trp Thr Ile Ala Ile Val Ala Val Leu Pro Leu Leu Gly
            20                  25                  30

Trp Asn
```

<210> SEQ ID NO 17
<211> LENGTH: 92
<212> TYPE: PRT
<213> ORGANISM: Bos taurus
<220> FEATURE:
<221> NAME/KEY: SOURCE
<222> LOCATION: 1..92
<223> OTHER INFORMATION: /mol_type="protein"
      /organism="Bos taurus"

<400> SEQUENCE: 17

Met Ser Glu Leu Glu Lys Ala Val Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Ser Asp
    50                  55                  60

Gly Asp Gly Glu Cys Asp Phe Gln Glu Phe Met Ala Phe Val Ala Met
65                  70                  75                  80

Ile Thr Thr Ala Cys His Glu Phe Phe Glu His Glu
                85                  90

<210> SEQ ID NO 18
<211> LENGTH: 92
<212> TYPE: PRT
<213> ORGANISM: Homo sapiens
<220> FEATURE:
<221> NAME/KEY: SOURCE
<222> LOCATION: 1..92
<223> OTHER INFORMATION: /mol_type="protein"
      /organism="Homo sapiens"

<400> SEQUENCE: 18

Met Ser Glu Leu Glu Lys Ala Met Val Ala Leu Ile Asp Val Phe His
1               5                   10                  15

Gln Tyr Ser Gly Arg Glu Gly Asp Lys His Lys Leu Lys Lys Ser Glu
            20                  25                  30

Leu Lys Glu Leu Ile Asn Asn Glu Leu Ser His Phe Leu Glu Glu Ile
        35                  40                  45

Lys Glu Gln Glu Val Val Asp Lys Val Met Glu Thr Leu Asp Asn Asp
    50                  55                  60

Gly Asp Gly Glu Cys Asp Phe Gln Glu Phe Met Ala Phe Val Ala Met
65                  70                  75                  80

Val Thr Thr Ala Cys His Glu Phe Phe Glu His Glu
                85                  90

<210> SEQ ID NO 19
<211> LENGTH: 94
<212> TYPE: PRT
<213> ORGANISM: Homo sapiens
<220> FEATURE:
<221> NAME/KEY: SOURCE
<222> LOCATION: 1..94
<223> OTHER INFORMATION: /mol_type="protein"
      /organism="Homo sapiens"

<400> SEQUENCE: 19

Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
            20                  25                  30

-continued

```
Glu Leu Lys Glu Leu Leu Gln Thr Glu Leu Ser Gly Phe Leu Asp Ala
            35                  40                  45

Gln Lys Asp Val Asp Ala Val Asp Lys Val Met Lys Glu Leu Asp Glu
        50                  55                  60

Asn Gly Asp Gly Glu Val Asp Phe Gln Glu Tyr Val Val Leu Val Ala
65                  70                  75                  80

Ala Leu Thr Val Ala Cys Asn Asn Phe Phe Trp Glu Asn Ser
                85                  90

<210> SEQ ID NO 20
<211> LENGTH: 94
<212> TYPE: PRT
<213> ORGANISM: Bos taurus
<220> FEATURE:
<221> NAME/KEY: SOURCE
<222> LOCATION: 1..94
<223> OTHER INFORMATION: /mol_type="protein"
      /organism="Bos taurus"

<400> SEQUENCE: 20

Met Gly Ser Glu Leu Glu Thr Ala Met Glu Thr Leu Ile Asn Val Phe
1               5                   10                  15

His Ala His Ser Gly Lys Glu Gly Asp Lys Tyr Lys Leu Ser Lys Lys
            20                  25                  30

Glu Leu Lys Glu Leu Leu Gln Thr Glu Leu Ser Gly Phe Leu Asp Ala
            35                  40                  45

Gln Lys Asp Ala Asp Ala Val Asp Lys Val Met Lys Glu Leu Asp Glu
        50                  55                  60

Asn Gly Asp Gly Glu Val Asp Phe Gln Glu Tyr Val Val Leu Val Ala
65                  70                  75                  80

Ala Leu Thr Val Ala Cys Asn Asn Phe Phe Trp Glu Asn Ser
                85                  90
```